(12) United States Patent
Hussey et al.

(10) Patent No.: US 8,556,177 B2
(45) Date of Patent: Oct. 15, 2013

(54) SYSTEM INCLUDING BAR CODED WRISTBAND

(75) Inventors: Robert M. Hussey, Waxhaw, NC (US); William H. Havens, Syracuse, NY (US)

(73) Assignee: Hand Held Products, Inc., Skaneateles Falls, NY (US)

(*) Notice: Subject to any disclaimer, the term of this patent is extended or adjusted under 35 U.S.C. 154(b) by 0 days.

(21) Appl. No.: 12/965,442

(22) Filed: Dec. 10, 2010

(65) Prior Publication Data

US 2011/0127325 A1 Jun. 2, 2011

Related U.S. Application Data

(62) Division of application No. 11/173,228, filed on Jun. 30, 2005, now Pat. No. 7,849,620.

(60) Provisional application No. 60/685,861, filed on May 31, 2005.

(51) Int. Cl.
*G06K 7/10* (2006.01)

(52) U.S. Cl.
USPC .................................................. 235/462.01

(58) Field of Classification Search
USPC .................................................. 235/462.01
See application file for complete search history.

(56) References Cited

U.S. PATENT DOCUMENTS

| | | | |
|---|---|---|---|
| 4,121,574 A | 10/1978 | Lester | |
| 4,476,381 A | 10/1984 | Rubin | |
| D297,939 S | 10/1988 | Bradbury et al. | |
| 4,814,759 A | 3/1989 | Gombrich et al. | |
| 4,818,850 A | 4/1989 | Gombrich et al. | |
| 4,835,372 A | 5/1989 | Gombrich et al. | |
| 4,850,009 A | 7/1989 | Zook et al. | |
| 4,857,716 A * | 8/1989 | Gombrich et al. | ............ 235/375 |
| 4,916,441 A | 4/1990 | Gombrich | |
| 5,006,830 A | 4/1991 | Merritt | |
| 5,071,168 A | 12/1991 | Shamos | |

(Continued)

FOREIGN PATENT DOCUMENTS

| WO | WO-9422098 A1 | 9/1994 |
|---|---|---|
| WO | WO-0003344 A1 | 1/2000 |

(Continued)

OTHER PUBLICATIONS

Agilent Technologies, Evolving Wireless Standards, Poster, Printed in U.S.A., May 11, 2004.

*Primary Examiner* — Daniel Hess
*Assistant Examiner* — David Tardif
(74) *Attorney, Agent, or Firm* — Heslin Rothenberg Farley & Mesiti P.C.

(57) ABSTRACT

A bar coded patient wristband identifies a patient wearing the wristband. The system comprises a bar code reader to read the bar coded wristband. A host computer is connected to the digital link to receive the segment of data from the bar code reader. A database correlates the segment of data to a patient to identify the patient. The patient wristband comprises a plurality of bar code symbols. A computer then retrieves a patient record from the database to identify the patient wearing the wristband. In one embodiment, a patient wristband for identifying a patient accepts a plurality of markings of 2 D bar codes distributed along the strip. In another embodiment, the wristband comprises a plurality of linear bar code lines and spaces distributed along the strip. The lines and spaces form a 1 D bar code.

26 Claims, 18 Drawing Sheets

(56) References Cited

U.S. PATENT DOCUMENTS

| | | |
|---|---|---|
| 5,153,416 A | 10/1992 | Neeley |
| 5,164,575 A | 11/1992 | Neeley et al. |
| 5,166,498 A | 11/1992 | Neeley |
| 5,179,569 A | 1/1993 | Sawyer |
| 5,193,855 A | 3/1993 | Shamos |
| 5,307,372 A | 4/1994 | Sawyer et al. |
| 5,381,487 A | 1/1995 | Shamos |
| 5,423,574 A | 6/1995 | Forte-Pathroff |
| 5,509,716 A | 4/1996 | Kolena et al. |
| 5,594,786 A | 1/1997 | Chaco et al. |
| 5,608,382 A | 3/1997 | Webb et al. |
| 5,640,301 A | 6/1997 | Roecker et al. |
| 5,689,229 A | 11/1997 | Chaco et al. |
| 5,694,919 A | 12/1997 | Rubsamen et al. |
| 5,757,021 A | 5/1998 | Dewaele |
| 5,765,875 A | 6/1998 | Rowley |
| 5,781,442 A | 7/1998 | Engleson et al. |
| 5,785,354 A | 7/1998 | Haas |
| 5,792,299 A | 8/1998 | Mosher, Jr. |
| 5,822,544 A | 10/1998 | Chaco et al. |
| 5,873,188 A | 2/1999 | Gehris |
| 5,880,452 A | 3/1999 | Plesko |
| 5,883,576 A | 3/1999 | De La Huerga |
| 5,967,559 A | 10/1999 | Abramowitz |
| 6,029,889 A * | 2/2000 | Whalen et al. ............... 235/380 |
| 6,032,155 A | 2/2000 | de la Huerga |
| 6,255,951 B1 | 7/2001 | De La Huerga |
| 6,259,355 B1 | 7/2001 | Chaco et al. |
| 6,346,886 B1 | 2/2002 | De La Huerga |
| 6,464,136 B2 | 10/2002 | Walsh |
| 6,510,634 B1 | 1/2003 | Riley |
| 6,618,602 B2 | 9/2003 | Levin |
| 6,671,563 B1 | 12/2003 | Engelson et al. |
| 6,731,989 B2 | 5/2004 | Engleson et al. |
| 6,747,561 B1 | 6/2004 | Reeves |
| 6,748,687 B2 | 6/2004 | Riley |
| 6,766,039 B1 | 7/2004 | Al-Sheikh |
| 6,779,024 B2 | 8/2004 | DeLaHuerga |
| 6,824,052 B2 | 11/2004 | Walsh |
| 6,830,180 B2 | 12/2004 | Walsh |
| 6,836,215 B1 | 12/2004 | Laurash et al. |
| 6,848,593 B2 | 2/2005 | Papp |
| 6,910,626 B2 | 6/2005 | Walsh |
| 2004/0186357 A1* | 9/2004 | Soderberg et al. ............ 600/300 |
| 2005/0040228 A1* | 2/2005 | Mullins et al. ................ 235/380 |
| 2006/0114986 A1* | 6/2006 | Knapp et al. ............ 375/240.01 |
| 2006/0267753 A1 | 11/2006 | Hussey et al. |
| 2009/0048870 A1* | 2/2009 | Godshall et al. ................. 705/3 |

FOREIGN PATENT DOCUMENTS

| | | |
|---|---|---|
| WO | WO-0199088 A1 | 12/2001 |
| WO | WO-0239412 A2 | 5/2002 |
| WO | WO-0241237 A1 | 5/2002 |
| WO | WO-02069099 A2 | 9/2002 |
| WO | WO-03009224 A1 | 1/2003 |
| WO | WO-03014871 A2 | 2/2003 |
| WO | WO-03025827 A1 | 3/2003 |
| WO | WO-03060805 A2 | 7/2003 |
| WO | WO-03085574 A1 | 10/2003 |
| WO | WO-03089313 A2 | 10/2003 |
| WO | WO-03090152 A1 | 10/2003 |
| WO | WO-03092769 A2 | 11/2003 |
| WO | WO-03100566 A2 | 12/2003 |
| WO | WO-2004028826 A2 | 4/2004 |
| WO | WO-2004042677 A1 | 5/2004 |
| WO | WO-2004044701 A2 | 5/2004 |
| WO | WO-2004061749 A2 | 7/2004 |
| WO | WO-2004081746 A2 | 9/2004 |
| WO | WO-2004088463 A2 | 10/2004 |
| WO | WO-2005054992 A2 | 6/2005 |
| WO | WO-2005057238 A2 | 6/2005 |

* cited by examiner

FIG. 4A - 4C 2D BAR CODES SHOWN WITH MAGNIFICATION

11.7-mil MicroPDF417

11.7-mil Truncated PDF417

25-mil Aztec Code 501 102

501 102

|  | MicroPDF417 | PDF417 | Aztec Code |
|---|---|---|---|
| Solves Wrap-Around Problem | ✓ | ✓ | ✓ |
| Reading Distance | Good | Good | Best |
| Tolerates Smudges & Smearing | ✓ | ✓ | ✓ |
| Data Accuracy | ✓ | ✓ | ✓ |
| Tolerates Registration Errors | | | ✓ |
| Pediatric Size | | | ✓ |

FIG. 6

Code 128
[5.0-mil]

3.0 to 5.0 in. (2.0 in.)

MicroPDF417
[11.7-mil]

1.5 to 7.5 in. (6.0 in.)

PDF417
[11.7-mil]

1.75 to 9.0 in. (7.25 in.)

Aztec Code
[25.0-mil]

1.0 to 9.0 in. (8.0 in.)

Code 128
[5.0-mil]

N.A.

MicroPDF417
[11.7-mil]

2.5 to 10.0 in. (7.5 in.)

PDF417
[11.7-mil]

2.25 to 10.5 in. (8.25 in.)

Aztec Code
[25.0-mil]

1.0 to 10.25 in. (9.25 in.)

SYSTEM INCLUDING BAR CODED WRISTBAND

CROSS REFERENCE TO RELATED APPLICATIONS

This application is a divisional of U.S. patent application Ser. No. 11/173,228, incorporated herein by reference in its entirety, which claims priority under 35 U.S.C. §119 of Provisional Application No. 60/685,861, filed May 31, 2005 entitled "Improved Bar Coded Wristband." The priorities of the above application Ser. No. 11/173,228 and Application No. 60/685,861 are claimed. The disclosure of the above Application No. 60/685,861, like the disclosure of application Ser. No. 11/173,228, is incorporated herein by reference in its entirety.

FIELD OF THE INVENTION

This invention relates generally to bar coded wristbands and more particularly to a system and method for reading bar coded wristbands without disturbing the wearer of the wristband.

BACKGROUND OF THE INVENTION

Wristbands can be used to identify individual persons wearing them. Typically wristbands have been cut from paper, plastic, or other bendable sheet type of material in the form of a strip. The strip can then be rolled to encircle a limb of the person, most typically the individual's wrist. Various fasteners or adhesives can be applied to maintain the physical presence of the wristband on the person. Techniques for fastening range from glue on paper wristbands to plastic or metal locking mechanisms used for higher security applications. Or, the band itself may include various types of cutout features so that when encircling the limb of a person a portion of the band can be inserted into the a receptacle slit or slot on the same band holding the band closed about the limb.

Common to all such applications is the ability to write, print, or otherwise mark the band with identifying information. In the least sophisticated applications of wristbands, a name or other identifying mark is simply written or printed on the band. Marking can be done by manually writing a name as with a pencil or pen, or information can be printed on a band by a machine such as a computer printer. In these most simple applications, the information is in a human readable form.

More recently bar codes, such as the UPC bar codes on most merchandise that we purchase have become a regular part of our every day life. Bar codes have also been added to wristbands in place of, or more typically in addition to human readable identifying information. Typically a special purpose band bar code writer applies a bar code to a wristband, in addition to other human readable information, such as a small photograph, a logo, or other human readable text. The bar code is typically designated a place on the band, allowing for other information to fill the remaining outside surface area of the band.

Bar coded wristbands are especially useful and helpful in institutional settings such as in hospitals. Such organizations generally utilize centralized or distributed computer systems that are amenable to providing at a minimum, individual person (patient) identification based on a scan of a patient wristband by a bar code scanner. Such identification can be particularly helpful to positively associate a particular patient to a particular hospital chart. Patient identification based on a scan of a patient wristband by a bar code scanner has also been used to automatically generate labels for patient specimens such as blood or urine. Patient identification has also been used to check and verify the dosage and types of medications administered to patients. Unfortunately, there are a series of problems associated with such bar coded wristbands. The problems are presented here in the context of a hospital setting, but as can be realized by others employing personal identification systems using bar coded wristbands. Many, if not all of these problems can be present in other institutional bar code wristband applications.

The first problem is that a linear bar code, a series of lines of varying thickness, a pattern familiar to most as similar to a merchandising product UPC code, is difficult to print on a wristband because of the width limitations of most typical bands. In one common scheme, a bar code is printed such that the lines of the bar code are roughly parallel to the limb encircled by the wristband (in the same direction of the arm, for example). Using this technique, the lines can be roughly as long as the narrow width of the strip that rolls into the wristband and the bar code can extend along the wristband, perpendicular to the limb. The problem with this bar code wristband arrangement is that the bar code then rolls around the wrist band. That is a bar code scanner trying to read such a bar code symbol views parts of the code at varying distances that can lead to depth field focus problems for the bar code reader optics package. To correct this problem, a nurse might have to try to flatten a portion of the bar coded section of wristband while attempting to scan it with a bar code reader. Or far worse, some of the code may be wrapped around the limb and not visible to the reader precluding a successful read. In this case, the wristband must typically be rotated and flattened to read it.

In response to this first problem, some linear bar coded wristbands use a 90 degrees rotated linear bar code such that the lines of the bar code are roughly perpendicular to the limb the band is wrapped around. In this case the length of the bar code (as determined by the number of lines the thickness of the lines, and the distance between them) is restricted to the narrow width of the wristband. While this solution generally exposes the entire code, thus solving the wrap around problem, such linear bar codes must be printed very small. A bar code scanner must have suitable optics to read such a small bar code and/or be placed very close to the bar code. Also, it is even more probable that the small bar code will not be in view thus requiring the person desiring to scan the code to rotate the wristband to bring the bar code into view for scanning. If the person to be identified is injured, sleeping, or otherwise immobilized, the task of rotating the wristband can be difficult. The possible consequences of manually rotating the band range from inconvenience and discomfort to worsening an injury.

Another problem with bar coded wristbands is that the code can become distorted, blurred, or otherwise unreadable. For example, a person tugging at the wristband or other physical damage to the wristband can cause pinching, creasing, tearing or other mechanical deformation. With a relatively weak plasticized band the code might become distorted under such conditions to a point where it is unreadable. Or, more likely a fluid, such as a bodily fluid, cleaning agent, or a medication, might spill on or be inadvertently rubbed against the code causing smearing, blurring, or even full or partial erasure of the code. Personal hygiene procedures in hospital settings, including showers and sponge baths can also degrade wristbands. When a patient ID wristband is damaged to a point where it needs to be replaced one or more nurses have to go to additional effort to reissue an ID wristband to the patient, thus wasting valuable hospital resources.

Another problem with bar coded wristbands is that they must be made small to be suitable for use with children and far smaller for infants. It can thus be seen that the above mentioned difficulties can become exacerbated when scaled to smaller pediatric wristbands.

Still another problem with bar coded wristbands is that there may be another copy of the same bar code printed on the wristband in a second location other than the wristband. For example, an identifying bar code on a patient wristband in a hospital can be identical to an identifying bar code on that patient's chart. In this case, a nurse desiring to conveniently scan a bar code might scan the bar code on the chart rather than the intended verification target bar code, the bar code on the patient's wristband. Some organizations solved this problem by adding characters to the identification string that distinguish the patient's wristband bar code from the bar code on the chart. This solution attempts to eliminate the possible error of incorrectly associating a patient with the wrong chart, thus incorrectly medicating or otherwise inadvertently treating the wrong patient. The Health Industry Bar Code (HIBC) provider application standard is an example of one such solution. The problem is that as previously presented, the space available for the bar code is barely sufficient for just the minimal amount of coded information simply to identify an individual person. Some institutions have eliminated the check characters in a misguided effort to make the bar code fit onto a wristband. However by doing this, they have actually increased the likelihood of a misread.

SUMMARY OF THE INVENTION

The solution to these problems is a system to read a bar coded patient wristband to identify a patient wearing the wristband. The system comprises a bar code reader to read the bar coded wristband. The bar code reader has a digital link to transmit a segment of data encoded in the bar code. A host computer is connected to the digital link to receive the segment of data from the bar code reader. A database is coupled to the host computer via a digital connection. The database correlates the segment of data to a patient record. A patient wristband comprises a plurality of bar code symbols. The plurality of bar code symbols contain information encoded into each bar code symbol. The bar code reader reads at least one of the plurality of bar code symbols and transmits the segment of data decoded from the at least one of the plurality of bar code symbols to the computer. The computer then retrieves the patient record from the database to identify the patient wearing the wristband.

A patient wristband for identifying a patient wearing the wristband comprises a substrate bendable strip. The strip is bendable into a wristband. The substrate strip accepts a plurality of markings of bar codes distributed along the strip. A closing mechanism creates a closed wristband from the bendable strip. The plurality of markings of 2 D bar codes distributed along the strip contain encoded information to identify the patient wearing the wristband.

In another embodiment of the patient wristband, the wristband comprises a substrate bendable strip. The strip is bendable into a wristband. The substrate strip accepts a plurality of linear bar code lines and spaces distributed along the strip. The lines and spaces are substantially aligned in a long narrow direction of the strip. The lines and spaces form a 1 D bar code. A closing mechanism creates a closed wristband from the bendable strip. The plurality of linear bar code lines and spaces distributed along the strip can be read by a bar code reader from substantially any direction around the wristband to identify the patient wearing the wristband.

DETAILED DESCRIPTION OF THE DRAWINGS

For a further understanding of these and objects of the invention, reference will be made to the following detailed description of the invention which is to be read in connection with the accompanying drawing, where:

FIG. 6 is a table rating the attributes of various 2 D bar codes;

DETAILED DESCRIPTION OF THE INVENTION

Figure 1:
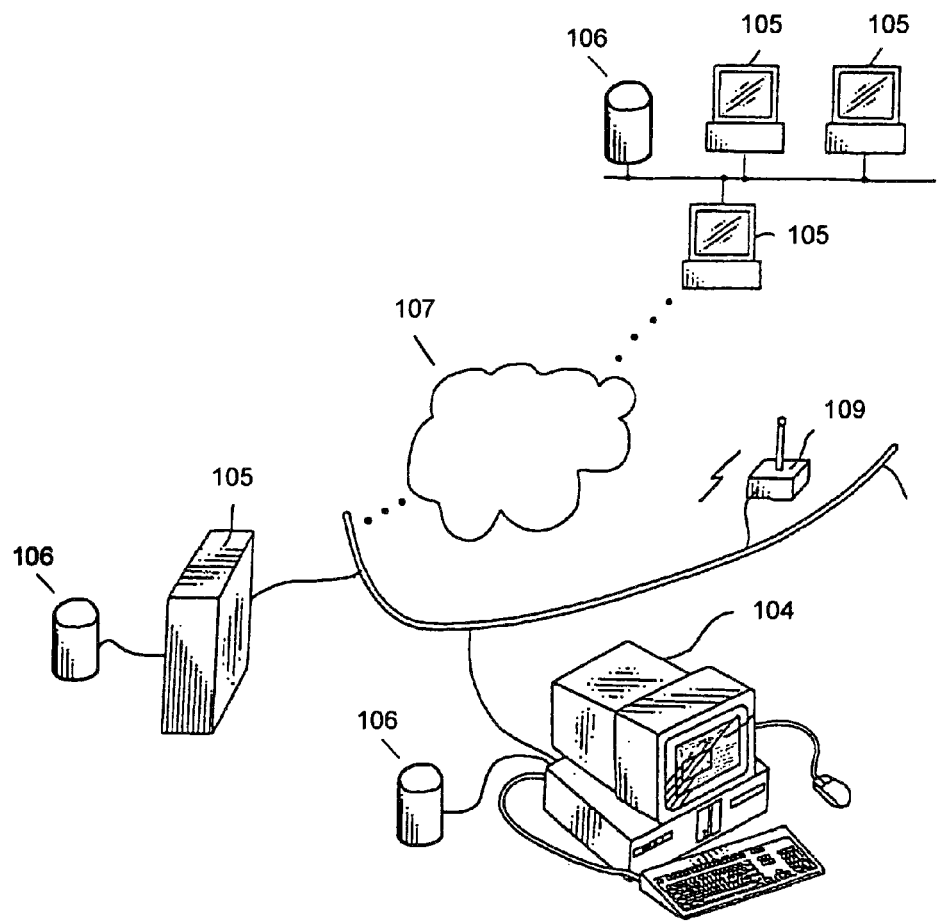
FIG. 1 shows one embodiment of the inventive system.
Figure 1:
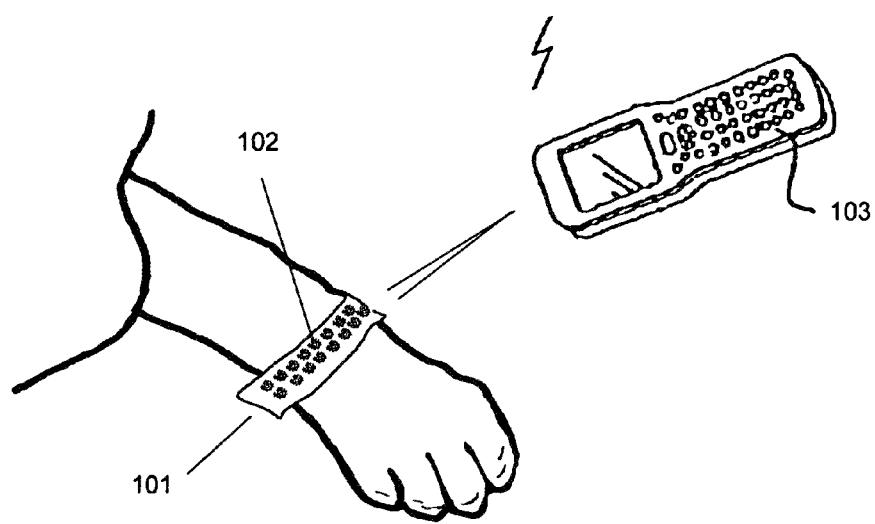
Figure 2A:
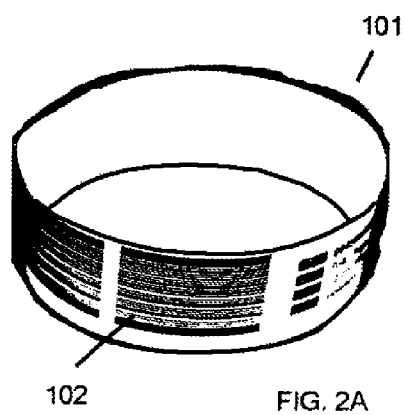
FIG. 2A shows a wristband using multiple broken 1 D bar codes.
Figure 2B:
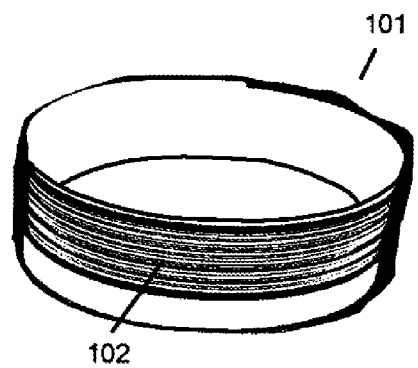
FIG. 2B shows a wristband using a continuous 1 D bar code.
Figure 2C:
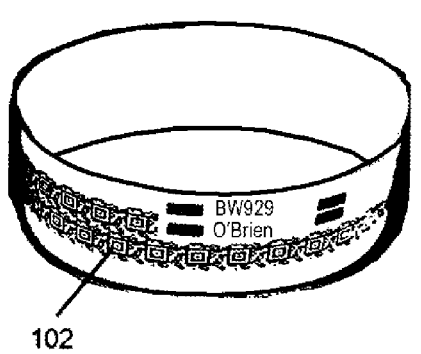
FIG. 2C shows a wristband using multiple Aztec 2 D bar codes.
Figure 2D:
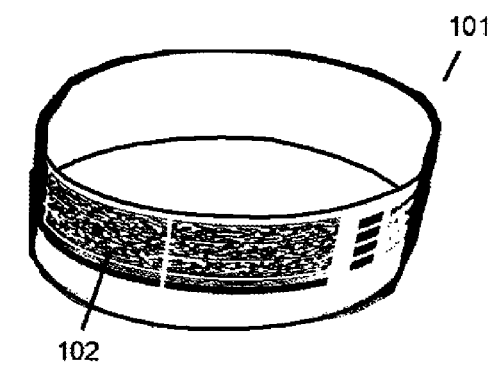
FIG. 2D shows a wristband using multiple PDF417 2 D bar codes.
Figure 2E:
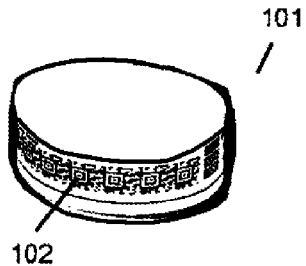
FIG. 2E shows a wristband using multiple Aztec 2 D bar codes.
Figure 2F:
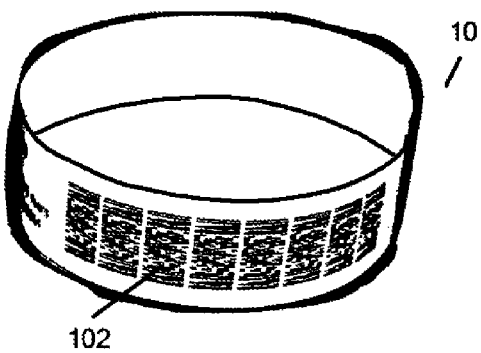
FIG. 2F shows a pediatric wristband using multiple Micro PDF417 2 D bar codes.

A system that solves the problem of providing a convenient and easy to read identifying bar coded wristbands for use in an institutional environment is shown in FIG. 1. The system is now described in the context of a hospital setting. Patient wristband 101 comprises a plurality of bar code symbols 102 situated across wristband 101. Each bar code symbol 102 can be an identical copy of each other. Preferably, bar code symbols 102 can be a plurality of 2D bar codes. FIGS. 2C to 2F show various embodiments of wristband 101 comprising 2D bar codes 102 of different types and different arrangements. FIG. 2C shows an embodiment using the Aztec code, FIGS. 2D and 2F show embodiments of wristband 101 using PDF417 and Micro PDF417 codes respectively, and FIG. 2E shows a small Aztec version for pediatric use. The advantages and disadvantages of the various embodiments of wristband 101 are discussed later in detail in this specification under the heading Bar codes for use on wristbands.

In another embodiment of FIG. 1, bar code symbols 102 can be printed in the form of an elongated linear bar code, such that the lines of the bar code are oriented roughly perpendicular to the member or limb around which they are wound. In this embodiment, the the aspect ratio of height to width of the 1 D bar code is greater than 1. Another way to describe this 1 D bar code is that with its "tall" bars (lines) and spaces that extend across the long dimension of the wristband, it is far higher than it is wide. In the elongated linear bar code embodiment of FIG. 1, the bar code lines can extend in a continuous or in a broken fashion around a substantial portion of the wristband. The broken fashion elongated linear bar code embodiment is shown in FIG. 2A, a continuous embodiment is shown in FIG. 2B.

The system further includes a bar code reader 103 to read the patient bar coded wristband 101. Bar code readers 103 of different types are variously suited for use with the different embodiments of wristbands 101. Specific types of bar code readers are discussed in more detail later in this specification. One or more bar code readers 103 communicate with computer 104 by any method suitable for digital communications between a bar code reader 103 and a computer 104. Where computer 104 is co-located with the bar code reader 103 communications options include hard wiring by serial, parallel, USB, Firewire, Ethernet, or other wired interface, copper wire, coaxial cable, optical fiber, twisted wire, shielded cable, or shielded twisted wire and wireless interfaces 109. Both wired and wireless interfaces 109 can further be connected to the Internet 107.

Suitable wireless standards as known in the art of digital wireless communication range from data over cell phone to personal area networks, including GSM (Global System for Mobile), GPRS (General Packet Radio Service), EDGE (Enhanced Data Rates for GSM Evolution), W-CDMA (FDD) (Wideband Code Division Multiple Access Frequency Division Duplex), TD-SCDMA (Time Division-Synchronous Code Division Multiple Access), HSDPA (High Speed Downlink), TIA/EIA-95A/B (cdmaOne System), cdma2000 (1xRTT) (1x Radio Telephone Technology), 1xEV-DO, (1x Evolution Data Only; High Rate Packet Data), 1xEV-DV, (1x Evolution Data and Voice), iDEN (Integrated Dispatch Enhanced Network), TETRA (Terrestrial Trunked Radio), Bluetooth (Wireless Personal Area Network; PAN), IEEE 802.11 a/g/h/j (Wireless Local Area Network; LAN), IEEE 802.15.3a (UWB), (Ultra Wideband Personal Area Network; PAN), IEEE 802.16a/e (Wireless Metropolitan Area Network (MAN). In addition to conventional amplitude (AM), frequency modulation (FM), frequency shift keying (FSK), and phase shift keying (PSK), other suitable data modulation types include GMSK, rotating 8PSK and higher, including $3\pi/8$ rotating 8PSK, QPSK, 16QAM through 128QAM and higher, M16-QAM and higher, $\pi/4$ DQPSK, GFSK, DBPSK, CCK with DQPSK, subcarrier OFDM, including 52 subcarrier OFDM, Shaped Pulse or Frequency switched OFDM, and OFDM with QPSK. Other wireless radio frequency (RF) interfaces or wireless light interfaces, including visible and infrared light (IR) LED or laser light sources and detectors, and other light operated interfaces including line of sight or fiber optic connections can be used as well.

In the case of a co-located computer 104, computer 104 can be a desktop PC, laptop PC, Notebook PC, Tablet PC, hand held PC, PDA, or other wired or wireless computer 104. Similarly, bar code reader 103 can further include computer 104. In this embodiment, computer 104 can communicate with other computers 105 via a wired or wireless connection. Such communication between a bar code reader 103 and computers 105 can take place by a direct wired or wireless communication between the computers or by connection to a computer network accessible to both computers 104 and 105.

Also included in the system is a database 106. Database 106 contains the data to correlate a patient's bar coded wristband 101 to the patient's information. The patient's information can include, the patient's identification ("ID"), a photograph or picture of the patient, other patient biometric identification information and any other patient records associated with that patient, including the patient's name, address, phone number, emergency contact information, prescription history, treating physicians, guardian or health proxy contacts, medical treatment history, medical insurance information, current prescription medications, medication history, and names of identifying physicians, etc. Database 106 is typically a relational database as known in the art, but could be any suitable database for correlating information as listed above to the patient wristband 101. It should be noted that a database 106 can also reside in any suitable type of memory within a PDT, including RAM, ROM, EPROM, EEPROM, hard drive, optical drive, or any suitable disk drive. Database 106 can also reside in and be attached to a bar code reader such as can be incorporated into a PDT, in the form of a drive or memory "stick", a portable plug in memory unit comprising solid state or rotating disk memory.

A nurse can use bar code reader 103 to scan wristband 101. Under the various embodiments of the invention, on approaching the patient, the wristband need only be in partial view. Because of the plurality of bar code indicia in the forms of groups of lines of linear code, continuous lines or linear code, or multiple 2D bar codes, the nurse merely aims the reader at the wristband from a suitable distance. Some alignment of the reader may be required when using older technology linear readers where that reader is suitable to a particular bar code 102. More commonly, bar code reader 103 can be a 2D imaging bar code reader that automatically reorients any symbol as needed in software. Such 2D imaging bar code readers 102 need merely capture at least one full or partial bar code symbol to identify a patient.

Figure 1A:
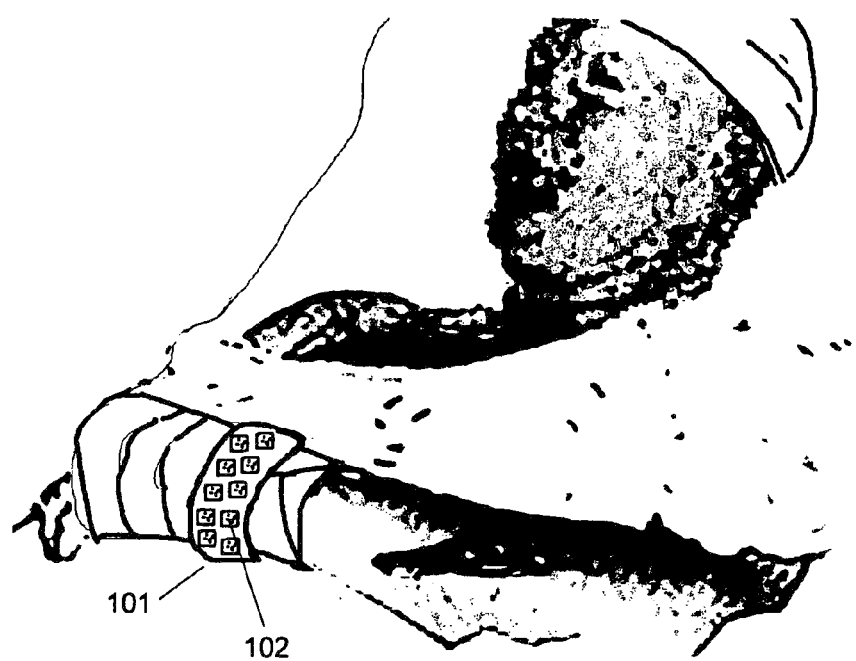
FIG. 1A shows a patient wearing an inventive bar coded wristband.

It can therefore be seen that an important aspect of the invention is that in the exemplary hospital setting, the nurse will likely not need to manipulate the patient in any way to expose a readable bar code symbol 102. The inventive system thereby reduces nurse fatigue and frustration leading to increased nursing efficiency. Use of the inventive system also can create a safer and more comfortable environment for the patient. For example as shown in FIG. 1A, in the case of a severely burned patient or a patient with multiple fractures or lacerations, it can be painful or further injurious to further move or manipulate a patient limb or other body part to expose a bar code wristband in order to scan it. Under the inventive system, no manipulation is required where even just a small portion of the wristband is in view.

It should be noted that the term "wristband" used in referring to wristband 101 is a traditional name for a wrap around identifying band. Wristband 101 can be wrapped around any limb of the patient on any part of the limb or otherwise affixed to a patient or clothes or dressings worn by the patient.

Once conveniently scanned, the coded information contained within a bar code symbol 102 can be relayed to computer 104. In the case where computer 104 is included in bar code reader 103, the digital information is conveyed internally within the body of bar code reader 103. Otherwise bar code reader 103 transmits the digital information decoded from bar code 102 to computer 104 by any suitable method, including the exemplary communication methods previously discussed.

Computer 104 can comprise database 106 and further correlate and return one or more pieces of information based on the decoded bar code data, or more likely computer 104 further communicates with other computers 105, such as by a suitable computer network. Similarly, one or more computers 105 may further comprise database 106, or database 106 can reside on a remote computer, such as a remote computer server on a local or distant computer network including the Internet 107. There may also be multiple databases 106 where some patient information such as ID and medications may be on one database 106 as on or associated with a computer 105 in the local hospital, whereas other patient data, such as patient treatment history, can be accessed on another database 106. In such cases, the one or more remote databases can be anywhere accessible by a computer network, such as anywhere on the Internet 107. The security of such a network can be enhanced by use of a virtual private network ("VPN") residing on the Internet. Various levels of VPN security can be implemented using a selection of private and public keys.

Following the connection to one or more databases 106, the patient information can be returned to computer 104 and displayed on a display associated with either computer 104 or on bar code reader 103 for the nurse to see. The nurse can view just the patient ID information or in some embodiments can further access other information associated with that patient as needed from one or more databases 106 using a user interface on either on bar code reader 103 or on computer 104. Such an interface can be graphical user interface ("GUI").

Patient identification based on a scan of the inventive patient wristband can be used to automatically generate labels for patient specimens including, but not limited to blood or urine.

The inventive wristband can also be used in an amusement park setting. Persons purchasing entry to the park or certain types of tickets authorizing certain rides and/or admission to events can be issued an identifying wristband. Entry into attractions, rides, or events could then be controlled by scanning the wristbands. For example, access to a water park at a particular amusement center might require payment of a higher ticket price. Only person's having a wristband reflecting the higher ticket fee would be granted admission to the water park. While patrons benefit from the ease of access to various attractions and facilities at the amusement park, the park can benefit by acquiring additional market research. Since the scanning results at each attraction can be added to a database, the park can gain valuable marketing information regarding visits to each attraction. Another advantage of issuing the inventive wristband to amusement park patrons is that missing children can more easily be reunited with their parents or guardians. On purchasing tickets, child IDs can be associated in the amusement park computer system with their adult supervisors, usually their parents, adult friends of the family, teachers, camp counselors, or older siblings. Certain personnel in the park, including park security guards, can be authorized to scan child wristbands to further help locate a particular child's supervisor for that park visit. In this application, it can be advantageous to exclude most human readable ID information from the wristband to help avoid undesired contact between the child attendees and strangers.

It should further be noted that other functions can be performed by the system. For example, a local computer can track a nurse's rounds while visiting a number of patients. Such tracking can be helpful in typical hospital settings where there is understaffing. Nurses caring for many patients can be automatically reminded if some pre-determined time has past without a visit to one or more patients. Or, such tracking can be used by nursing or other medical managers to review the frequency of patient visits. Information regarding a scan of bar code 102 on wristband 101 could also be sent to other data bases indicating the patient visit or admission to a particular institution on a particular date.

It can now be seen that a system to read a bar coded patient wristband to identify a patient wearing the wristband can comprise a bar code reader to read the bar coded wristband; a housing to hold the bar code reader; a computer contained within housing, the computer connected to the bar code reader to receive the segment of data from the bar code reader; a database contained within the housing and coupled to the computer, the database to correlate the segment of data to a patient record. A patient wristband comprises a plurality of bar code symbols, the plurality of bar code symbols containing information encoded into each bar code symbol, wherein the bar code reader reads at least one of the plurality of bar code symbols, the bar code reader transmitting the segment of data decoded from the at least one of the plurality of bar code symbols to the computer, and the computer retrieving the patient record from the database to identify the patient wearing the wristband. The database in the housing can be updated by a host computer using a digital link to the computer in the bar code reader. The database in the housing can further be updated by a host computer outside of a hospital using a computer network connected to the computer in the bar code reader housing. The computer network is the Internet. A digital link can be a wireless digital link chosen from links such as those using GSM, GPRS, EDGE, W-CDMA (FDD), HSDPA, TIA/EIA-95A/B, cdma2000, 1xEV-DO, 1xEV-DV, iDEN, TETRA, Bluetooth, PAN, IEEE 802.11 a/g/h/j, LAN, WAN, IEEE 802.15.3a, IEEE 802.16a/e, or MAN. The digital link further make use of the Internet. The digital link can also include a wired digital link such as copper wire, coaxial cable, optical fiber, twisted wire, shielded cable, and shielded twisted wire. The digital link can also be a serial links consisting of RS-232, RS-485, parallel, USB, Ethernet, and Firewire. The information that can be encoded into each bar code symbol can include information consisting of patient ID, patient name, patient address, current prescription medications, prescription history, medication history, and names of identifying physicians. The information encoded into each bar code symbol can comply with the HIBC standard indicating the type of data encoded and intended placement of the information on a patient wristband. The information encoded into each bar code symbol can incorporate a Health Industry Number (HIN) that identifies the institution that affixed the wristband. The host computer can alert that a patient is overdue for a visit by a hospital employee. A host computer monitor scans of patient wristbands and make a report including patient visitation information to a hospital supervisor. The bar code reader can be a PDT. The PDT can further comprises a card reader for reading indicia on an ID card. The indicia on the ID card can be stored in a magnetic stripe and the card reader is a magnetic stripe card reader. The PDT can further comprises a biometric sensor to identify and grant PDT access to an identified and authorized user. The biometric sensor can be a fingerprint sensor. The PDT can further comprise a UV lamp to illuminate organs to highlight a pathological condition. The UV lamp can be a UV LED. The PDT can further comprise a microphone to record voice signals using the PDT. The microphone can be a wireless microphone. The wireless microphone can communicate according to the Bluetooth wireless communication standard. The PDT can include a chemical sensor or electronic nose to analyze chemicals emitted from a human organ. The bar code reader can be a hand held bar code reader in a hand held housing. The hand held housing can contain a battery. The bar code reader can be battery operated, including a hand held battery operated PDT bar code reader.

While the invention has so far been described in terms of a hospital patient, it should be noted that the inventive system including a wristband with multiple bar codes can also be used with animal in a veterinary setting, such as in an animal hospital. Small pediatric wristbands according to the invention, such as those using the Aztec code, are particularly well suited for use with small animals.

Bar Codes for Use on Wristbands:

A one dimensional ("1 D") linear bar code typically encodes data into a series of parallel lines of varying thickness. An example of a 1 D bar code is the "interleaved 2 of 5 code". This code uses a combination of wide and narrow bars and wide and narrow spaces between the bars to encode typically numeric data. This bar code is said to be interleaved because some of the numbers are encoded by the dark lines while others are encoded by the spaces. Another suitable 1 D barcode type is code 39. Code 39 is slightly more secure and offers alpha numeric (characters plus numbers) encoding. Code 128 can also be suitable as a usable 1 D bar code type. While it can be possible to read a 1 D bar code at a slight angle from a line running perpendicular to the bars of the bar code, there is only one set of information that is encoded into the bar code in one dimension.

Figure 3A:
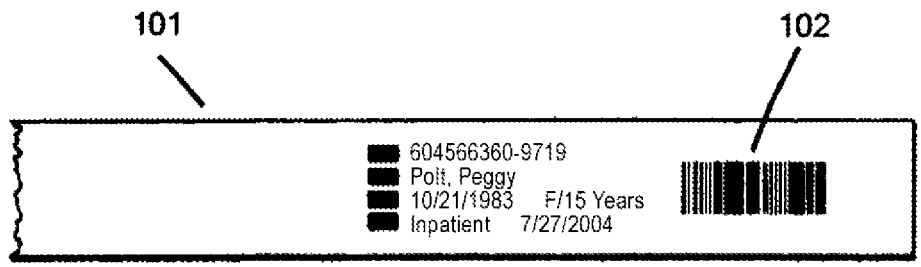
FIG. 3A shows a wristband using a 1 D bar code.

The x direction of a 1 D bar code is the length wise direction across which it is read. The X-dimension is the narrowest bar or space element used in a 1 D bar code. It is generally good practice to size the X-dimension relatively large at between 10 and 20 mils (1 mil=$\frac{1}{1000}^{th}$ of an inch). This allows for greater reading distances and better ease-of-use. FIG. 3A shows a wristband 101 using a single code 39 1 D bar code 102 according to the prior art. In order to accommodate the relatively long bar code 102, the x direction of the bar code is typically aligned with the length of the wristband.

There are several problems associated with wristbands 101 of the style shown in FIG. 3A. First it is likely that the wristband might roll so as to make part or all of the code out of line of sight view of a bar code reader. This type of 1 D bar code design is so long that the code bends around the wristband. Thus even if all of the code is in view, the ends of the code will still be at a greater distance from the reader than the center of the code. It can be more difficult for a bar code reader to read such a bent or rolled code, than to read a 1 D bar code on a flat surface. Also, if a portion of the ID bar code is wrapped around so that is out of view, the bar code can not be read.

Figure 3B:
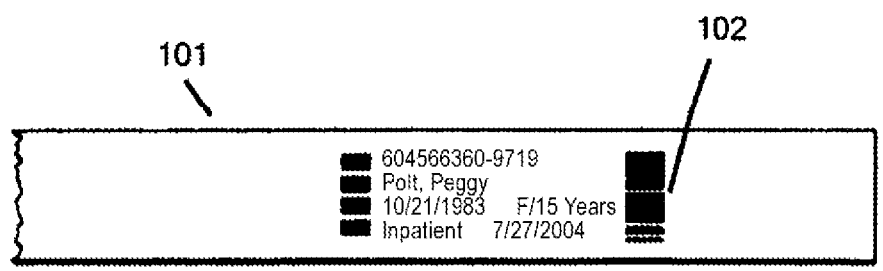
FIG. 3B shows a wristband using a rotated 1 D bar code.

A partial solution to the problem of rolled 1 D bar codes has been accomplished by rotating the bar code 90 degrees as shown in FIG. 3B. Here, the x direction of the 1 D code is perpendicular to the long dimension of the wristband. But, in order to fit the code to the short dimension or the width of a typical wristband, the X dimension must be reduced to about 5 mils The small X dimension causes the bar code reading distance to become very small. The reader must be oriented much closer to the bar code on the wristband and also must be positioned more accurately for a successful read. Moreover, the tiny bar code symbol is far more susceptible to smearing and smudging that can cause the bar code to become unreadable. While, the 90 degree rotated bar code solution prevents the bar code from bending or wrapping around the wristband, there is a high likelihood that the tiny bar code on the wristband will roll out of view. Thus, this version is both more difficult to read it is far more likely that there will need to be some manipulation of both the wristband and wearer's limb to bring the symbol into view.

Two-dimensional ("2 D") bar codes achieve far higher efficiency than 1 D codes by encoding data across a surface. Also, for a given amount of marking space, a larger X-dimension can be used giving longer reading distances. Another advantage of 2 D bar codes is that many of them employ Reed Solomon error correction schemes making them far more reliable than the older 1 D bar codes.

Figure 4A:
FIG. 4A shows a Micro PDF417 2 D bar code.
Figure 4B:
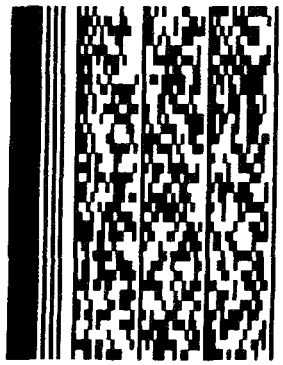
FIG. 4B shows a Truncated PDF417 2 D bar code.

MicroPDF417 is one of the more space-efficient stacked 2 D bar codes. Stacking refers to the rows coding marks placed on top or each other. Exemplary MicroPDF417 2 D bar code symbols are shown in FIGS. 4A and 4B. A typical MicroPDF417 symbol of 2 columns by 8 rows can have overall dimensions of 0.642×0.280 inches.

PDF417 is one of the most popular of the stacked two-dimensional bar codes. It offers more flexibility in choosing a particular error correction level ("ECL"). A higher ECL is a more robust design. With higher ECLs, all encoded data can still be retrieved from partially damaged symbols. At an X-dimension of 11.7 mils and a row height of 3× (three times the X-dimension) a PDF417 symbol can still fit on a 1" wristband. Because of the powerful Reed Solomon error coding, with a ECL of 5 a bar code reader need only view about 0.805" by 0.210 inches of the entire symbol to completely decode the encoded data. ECLs of 4 to 6 can be used in typical wristband applications.

Most 2 D bar codes, including PDF417 bar codes have a quiet zone requirement. This is an area around the bar code that must be clear (generally white, but otherwise free of the dark spots, blocks, or bars used as part of 1 D or 2 D bar codes. PDF417 has a quiet zone requirement of 2× clear all around the perimeter of the symbol. Without the required clear zone, error free reading can be impossible. Thus, PDF417 bar codes cannot be printed close enough to touch each other on any side. They should be placed no closer than the 2× minimum spacing.

Figure 5A:
FIG. 5A shows a 2 D bar code with an L shaped perimeter reference.
Figure 5B:
FIG. 5B shows an Aztec 2 D bar code with a central reference.

The quiet zone requirement comes about to preserve a minimal frame of reference for a reader's image processing software to use in identifying and reading bar codes. This frame of reference can also be referred to as a finder pattern. Typically, as in PDF417 bar codes, one or more reference lines are printed on an outer edge of the bar code symbol as the finder pattern. This aspect of bar code reading is shown by the contrasting examples of FIG. 5A and FIG. 5B. FIG. 5A shows a generic 2 D bar code using an "L" shaped reference line finder pattern 501 along two sides of the perimeter of the symbol. It can thus be seen that to preserve both identification of the type of symbol as well as to allow the image processing software in a bar code reader to properly process an image of the "L" based symbol, there will need to be a quiet zone adjacent to the "L" perimeter, typically between 1× and 3×. FIG. 5B shows an Aztec symbol having an internal bulls-eye finder pattern 501. Because the reference completely contained within the symbol, no quiet zone is needed. Therefore Aztec 2 D bar codes can be printed immediately adjacent to each other with 0× spacing (no quiet zone).

Figure 4C:
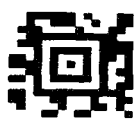
FIG. 4C shows an Aztec 2 D bar code.

The Aztec code, as shown in FIG. 4C, is among the most space-efficient of bar codes. An X-dimension of 25 mils gives a good balance of code size and reading distance. The 25 mil Aztec code of FIG. 4C encodes 13 characters into an area of about 0.375"×0.375" in total size. As shown in the examples below, it is an ideal 2 D symbol for use on a multiple bar code wristband since the symbols be printed one after another with no quiet zone.

For pediatric wristband applications, a very narrow and short wristband is still large enough to include a single row of contiguous or closely spaced Aztec symbols. Or, for adult wristband applications, there is enough room to print two rows of symbols, one over the other. When using multiple rows of Aztec symbols, symbols in one row can be offset by about half of the distance across a single symbol, from those on the adjoining row. This spacing further increases the likelihood that a given symbol on a wristband will be in convenient view to a nearby bar code reader and that the wristband will not need to be manipulated to read one of the codes.

FIG. 6 shows a grid of some of the problems associated with patient wristbands, including wrap around, reading distance, smudges and smearing, data accuracy, registration errors, and ability to size to a pediatric wristband. The ability of the codes MicroPDF417, PDF417, and the Aztec codes are shown by check marks and the words good or best. It can be seen that Aztec codes are a preferred 2D bar code for wristband applications according to the invention.

Another 2D code, Data Matrix, can be used as an alternative to the Aztec code, but Data Matrix does have a 1× perimeter clearance requirement. Also, because it uses a perimeter reference scheme in the form of a peripheral finder pattern, Data Matrix bar codes are far more susceptible to damage along the edges then are Aztec symbols. As will further be shown in the wristband examples below, it is common for the cutting or scoring operation to partially remove one side of a bar code symbol or an entire row of bar code symbols, rendering edge referenced symbols un-readable.

Wristbands having a plurality of substantially identical bar codes or a plurality of various types of bar codes having substantially the same information encoded into each bar code can appear in various colors. The bars of the bar codes (markings of 2D bar codes) have a low level of reflectivity and the substrate has a higher level of reflectivity for a given illumination wavelength (illumination color). For example, typical bar code readers see black, blue, or green as bars (markings of 2 D bar codes) and red or white as the substrate or spaces when using red illumination. Thus dark bar code sections can be printed in black, blue, green, and various shades thereof. Such colors can have human readable meanings as in a hospital triage scheme where the colors can represent levels of triage. Similarly, red can be used on the wristband substrate in place of white for reasons unrelated to the encoding of data into the plurality of bar code symbols on a wristband and will appear as a highly reflective background to most bar code readers.

Figure 18:
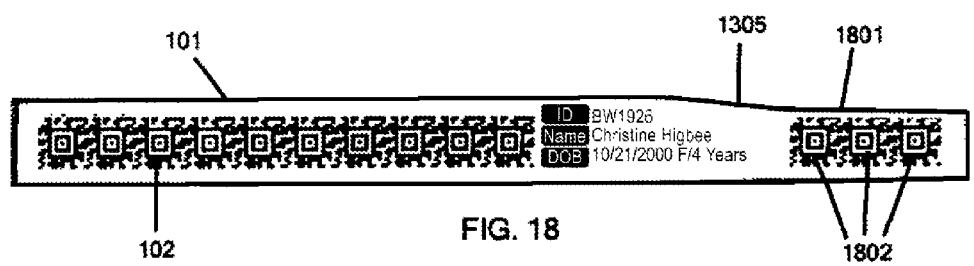
FIG. 18 shows a tapered pediatric wristband with multiple Aztec 2 D bar codes.

Printing wristband strips can be problematic, particularly where codes with edge finding patterns are used. Care must be taken to feed and maintain alignment of the strip during the printing process such that no finding patterns are truncated by a miss-feed where the strip prints off to one side or the other. Such registration problems are far less critical where Aztec 2 D symbols using bulls-eye finding patterns are used. Example 11 discusses a truncated Aztec symbol caused by a printing miss-feed as shown in FIG. 18.

Bar coded wristbands according to the invention can be thermally printed on plastic substrate strips as known in the art. In a hospital setting, a thin white plastic strip is generally used. Such strips are commercially available from the Zebra Corporation, General Data Corporation, and Precision Dynamics Corporation (also known as the PD Corporation). Exemplary wristband substrates are shown in FIGS. 13, 14, 15, and 16A and 16B. The substrate strip can also be a part of a larger strip for convenience in feeding through a printer. The larger strip can be scored to create a smaller shaped strip. The printed substrate strip that is to become the wristband can then be conveniently removed from the larger strip. A wristband so printed is shown later in FIGS. 16A and 16B in example 9.

Strips are also available that can be peeled from a backing strip to expose a section of adhesive backed wristband to close and affix the wristband about a limb. Or, strips can be pre-scored or pre-punched with holes for affixing the wristband. A wristband with pre-punched holes is shown FIG. 13 and discussed in further detail in example 6. Such strips can be fastened by a filament of string or wire, a plastic rivet, or by a metal fastener, such as a metal rivet. Thus it can be seen that the fastener can be a string, thread, wire, plastic filaments, tie wraps, plastic rivet, metal rivet, plastic clip, plastic screw and nut, metal screw and nut, and metal clip.

In less demanding or emergency situations, the inventive bar coded wristbands can be printed on paper or other less durable materials than plastic. For the highest security and most demanding applications, the inventive wristband can be made from a sheet of carbon fiber based material, woven material, or from sheet metal. When formed from sheet metal, care should be taken to further roll or coat the edges to prevent injury to the limb to which the wristband is affixed. A metal or fiber based substrate can be suited to accept some types of marking inks or other marking methods such as etching or engraving where the raised portions of the symbols are darkened for reading by a bar code reader. Or, a plastic strip can be glued or otherwise affixed to the metal or fiber based substrate, the plastic strip to accept the bar code markings by a conventional printing method. More sturdy wristbands according to the invention might also be needed in some military applications such as in battlefield hospital in or near an active war zone. Thus, barcoded wristbands according to the invention can be formed from plastic, paper, mylar, aluminized mylar, foil, metal foil, metal, woven nylon, and woven cloth.

It should also be noted that bar coded wristbands according to the invention can further incorporate the Health Industry Bar Code (HIBC) provider application standard. The provider application standard can provide enhanced interoperability through standardization in a networked hospital environment. The standard suggests data structures for bar code encoded patient data and adds two data "flags" to the data. The flags indicate what encoded data is and where it was scanned from. The standard is intended to help prevent mistakes such as those caused by scanning a chart instead of the patient's wristband.

2 D bar coded wristbands according to the invention can also further incorporate the Health Industry Number (HIN). This additional data, in the form of a second field, can be used to identify the health care provider location where the wristband was affixed on the patient. Use of the HIN field can help patients who are transferred from one location to another, such as those transferred from a remote clinic or an ambulatory surgical site.

Bar Code Readers and Compatibility:

There are four classes of mobile bar code readers that can decode 2 D bar codes: linear imagers, area imagers, linear lasers, and raster lasers. Some linear scanners can read stacked two-dimensional codes, such as MicroPDF417 and PDF417. Area imagers can read stacked and matrix bar codes. Area imagers can take a digital picture of the bar code symbol and use software algorithms to find and decode the bar codes in the image. The software can read codes at any angle, making the decoding process more convenient. Raster lasers can read linear and stacked 2 D bar codes, but they can not read 2 D codes such as Aztec. Only area imagers can read 2 D matrix codes.

Figure 7A:
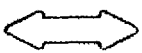
FIG. 7A shows usable 2 D bar code reading distances for an exemplary SF type of 2 D bar code readers.
Figure 7A:
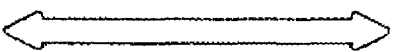
Figure 7A:
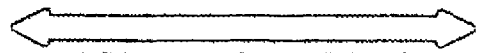
Figure 7A:
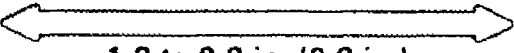
Figure 7B:
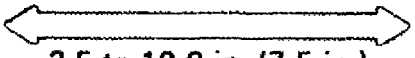
FIG. 7B shows usable 2 D bar code reading distances for an exemplary SR type of 2 D bar code readers.
Figure 7B:
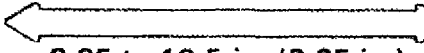
Figure 7B:
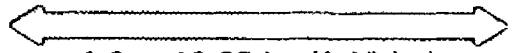

An exemplary image scanner suitable for reading the inventive patient bar coded wristbands is the IT4100 manufactured by Hand Held Products Corporation. The IT4100 is available with two optics packages, the short focus "SF" model and the standard range "SR" model. FIG. 7A shows suitable 2 D bar code reading distances for the exemplary SF type of 2 D bar code readers. FIG. 7B shows suitable 2 D bar code reading distances for the exemplary SR type of 2 D bar code readers.

Other types of suitable bar code readers include various types of portable data terminals (PDT). Various security issues can also be addressed where PDTs are used in this application. Both topics are discussed in more detail in the section "Other Bar code reader types and Security Issues".

Wristbands:

The following examples are prints or line drawings of several different embodiments of wristbands having multiple bar codes. Most are prints or line drawings of actual multiple bar code symbol wristbands made by thermal printing on plastic strips.

Example 1

Figure 8:
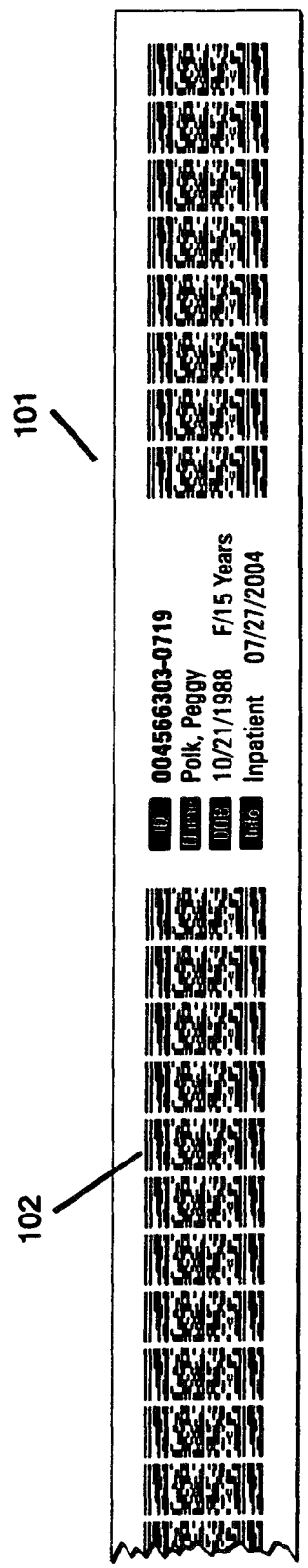
FIG. 8 shows a wristband with multiple 2 D Micro PDF417 bar codes.

FIG. 8 shows an inventive wristband 101 with multiple 11.7 mil MicroPDF417 2 D bar codes 102. In addition to the multiple 2 D bar codes, there is a small break for human readable information. In practice such breaks should be minimized in order to preserve the high likelihood that a symbol will be in view for a bar code reader without needing to manipulate the wristband.

Example 2

Figure 9:
FIG. 9 shows a wristband with multiple PDF 417 2 D bar codes.

FIG. 9 shows an inventive wristband 101 with multiple 11.7 mil Truncated PDF417 2 D bar codes 102. Again, In addition to the multiple 2 D bar codes, there is a small break for human readable information. In practice such breaks should be minimized in order to preserve the high likelihood that a symbol will be in view for a bar code reader without needing to manipulate the wristband.

Example 3

Figure 10:
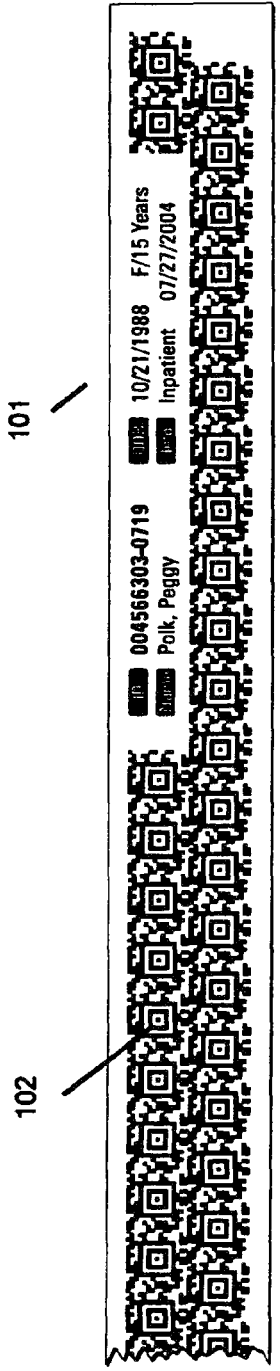
FIG. 10 shows a wristband with multiple Aztec 2 D bar codes.

FIG. 10 shows an inventive wristband 101 with two offset rows of multiple Aztec symbols 102. In addition to the multiple 2 D bar codes 102, there is a small break for human readable information. In practice, even small breaks should still be minimized in order to preserve the high likelihood that a symbol will be in view for a bar code reader without needing to manipulate the wristband. A single row of Aztec symbols continues without break under the human readable information.

Example 4

Figure 11:
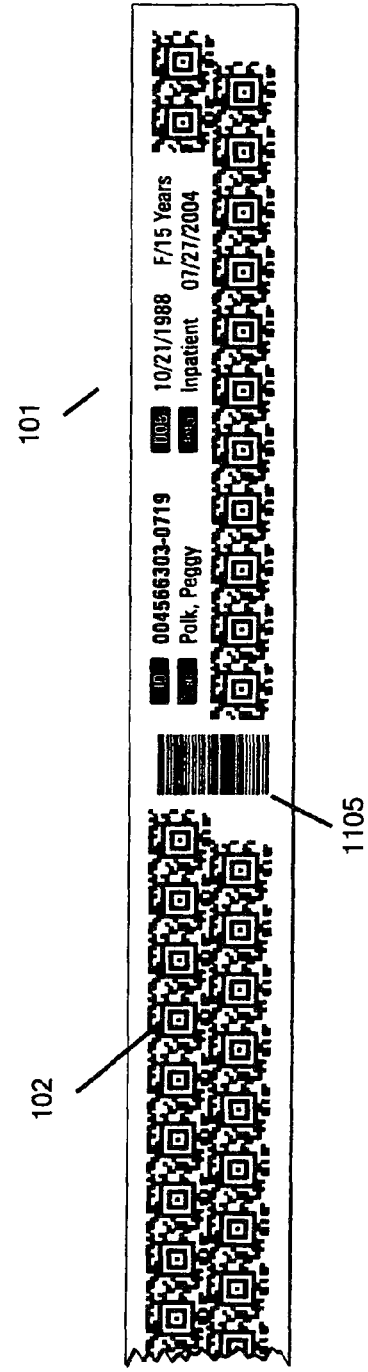
FIG. 11 shows a wristband with multiple Aztec 2 D bar codes and a 1 D bar code.

FIG. 11 shows an inventive wristband 101 with two offset rows of multiple Aztec symbols 102. In addition to the multiple 2 D bar codes, there is a small break for human readable information. This exemplary band is identical to the one of FIG. 10, except that it additionally includes one or more bar codes 1105 of a second type of 1 D bar code (one is shown in the example). A "backward compatible" wristband 101 as shown in FIG. 11 can be used in applications where available bar code readers can only read 1 D bar codes and not 2 D bar codes such as the Aztec codes shown in FIG. 11. Even with one or more instances of 1 D bar codes, the likelihood of a good read without wristband manipulation remains high everywhere along the length of the band.

Example 5

Figure 12:
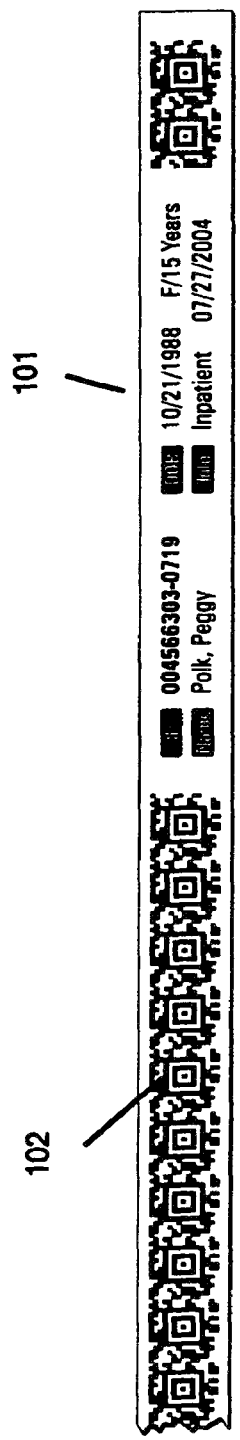
FIG. 12 shows a pediatric wristband with a single row of multiple 2 D Aztec bar codes.

FIG. 12 shows an inventive wristband 101 with a single row of multiple Aztec symbols 102. This is a narrow wristband that can be used for pediatric use. In addition to the multiple 2 D bar codes, there is a small break for human readable information. In practice such breaks should be minimized in order to preserve the high likelihood that a symbol will be in view for a bar code reader without needing to manipulate the wristband.

Example 6

Figure 13:
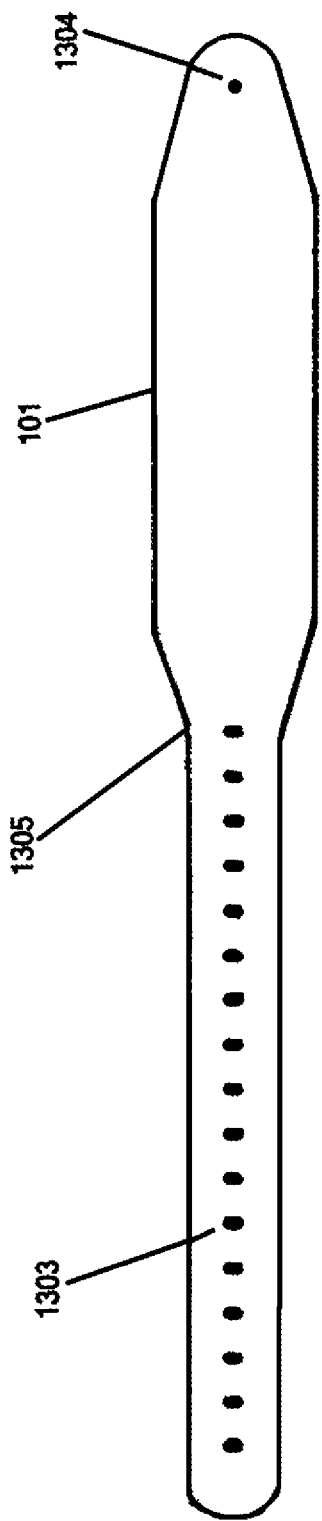
FIG. 13 shows a wristband substrate suitable for securing the wristband to a limb.

FIG. 13 shows a suitable substrate for use with the inventive wristband. One advantageous feature is the combination of the line of multiple holes 1303 for mating with hole 1304 in order to fasten the wristband about a limb. The fastener (not shown) can be of plastic, nylon, metal, or other suitable fastening material. Both the strength of the band and fastener needed can depend on the application. For example, an ID wristband at a county fair might be held in place by a string, while an ID wristband in a high security prison infirmary can be a metal rivet or clasp fastened with a clamping or riveting tool. Another advantageous feature of the wristband of FIG. 13 is taper 1305 that reduces the width of the band where a larger width is not needed for machine or human readable identifying printing. This wristband marks can further include an identifying logo, such as the symbol of an infantry company in a wartime battlefield infirmary setting (not shown).

Example 7

Figure 14:
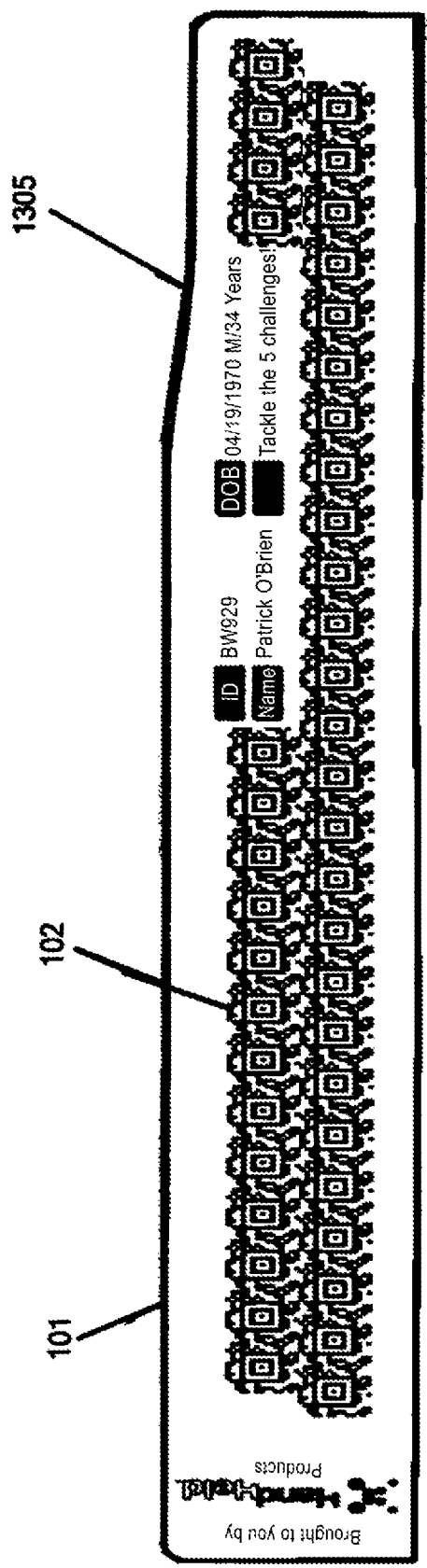
FIG. 14 shows a tapered wristband with multiple Aztec 2 D bar codes.

FIG. 14 shows an inventive wristband 101 with two offset rows of multiple Aztec symbols 102. In addition to the multiple 2 D bar codes, there is a small break for human readable information. In practice, even small breaks should still be minimized in order to preserve the high likelihood that a symbol will be in view for a bar code reader without needing to manipulate the wristband. A single row of Aztec symbols continues without break under the human readable information. This wristband further illustrates the use of the advantageous taper 1305.

Example 8

Figure 15:
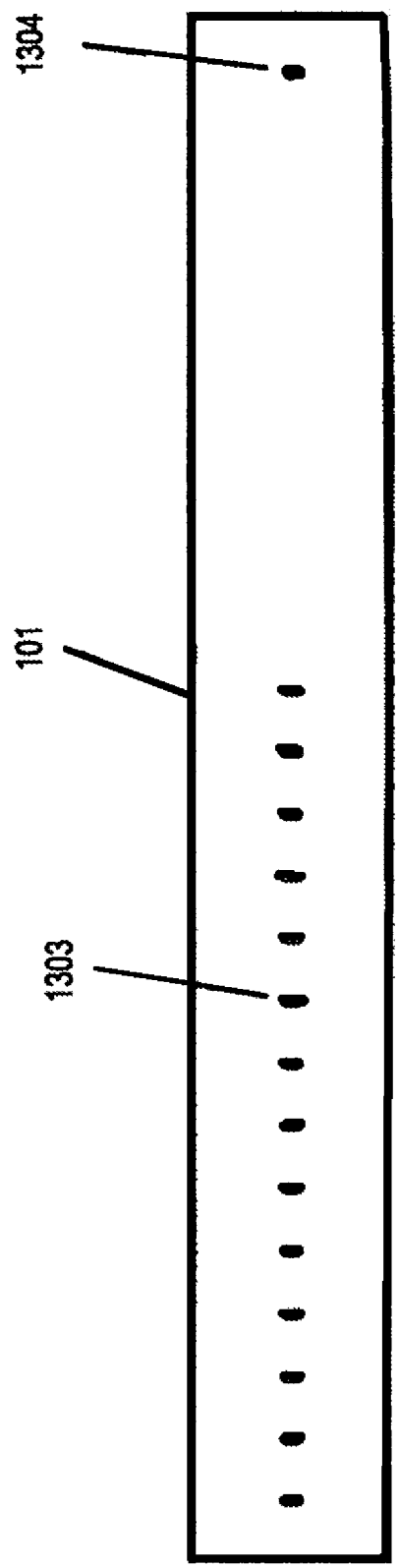
FIG. 15 shows a wristband substrate suitable for securing the wristband to a limb.

FIG. 15 shows a substrate suitable for use with the inventive wristband 101.

Example 9

Figure 16A:
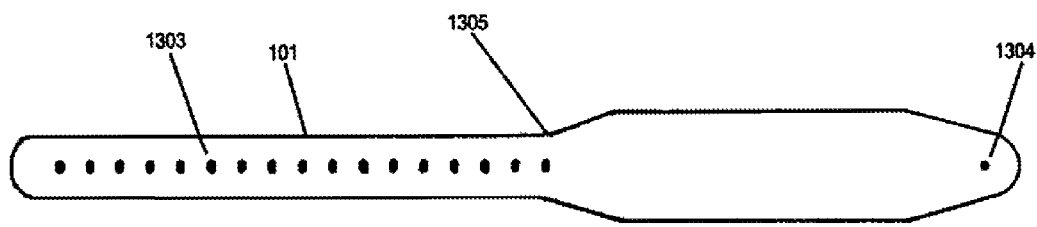
FIG. 16A shows a tapered wristband substrate suitable for securing the wristband to a limb.
Figure 16B:
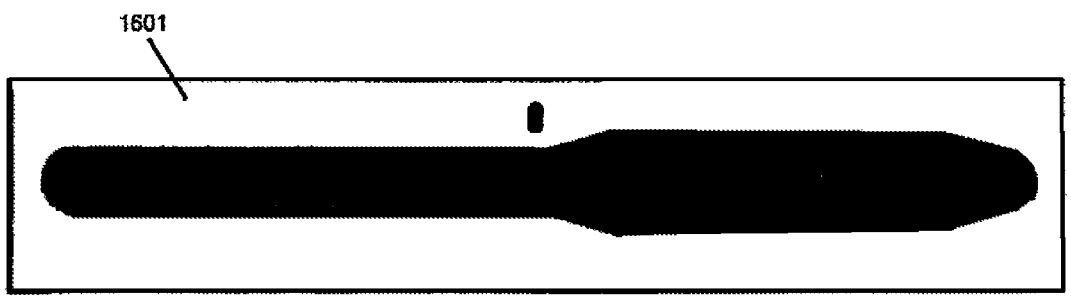
FIG. 16B shows a tape strip in which the bar code of FIG. 16A can be printed.

FIG. 16A shows a substrate suitable for use with the inventive wristband 101. FIG. 16B illustrates how a wristband with bar codes can be printed on a standard width of plastic and then cut from the strip 1601 to form the wristband. Such wrist bands can be rectangular, rounded, or tapered as show in FIG. 16A. The strip of plastic can be thermally printed by methods and equipment well known in the art.

Example 10

Figure 17:
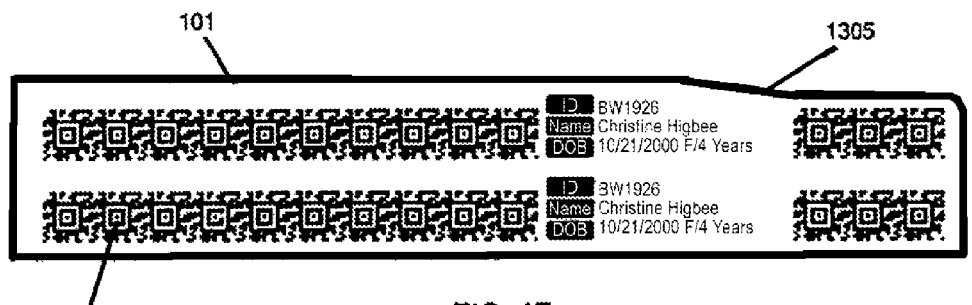
FIG. 17 shows a tapered wristband with multiple Aztec 2 D bar codes.

FIG. 17 shows an inventive wristband 101 with two rows of multiple Aztec symbols 102. In addition to the multiple 2 D bar codes, there is a small break for human readable information. Even with one or more instances of small breaks for text and or images, the likelihood of a good read without wristband manipulation remains high. With its short length, this wristband can be well suited for children.

Example 11

FIG. 18 shows an inventive wristband 101 with single row of multiple Aztec symbols 102. In addition to the multiple 2 D bar codes, there is a small break for human readable information. Additionally, there is a taper feature 1305. FIG. 18 further illustrates the inadvertent removal of a portion of the Aztec symbols in the section 1801 of the wristband following taper 1305. However, because the Aztec symbol is not an edge referenced signal, these damaged symbols 1802 are still completely readable using the standard Aztec error correction scheme with suitable ECL. Thus, the likelihood of a good read in this case without wristband manipulation remains high. With its short length and narrow width, this wristband can be well suited for pediatric use.

Other Bar Code Reader Types and Security Issues:

A portable data terminal (PDT) can be particularly convenient for use with wristbands having multiple bar codes. A PDT can be differentiated from a simple optical reader as offering among other features, expanded computational capabilities. A PDT running a portable computer operating system typically includes a user entry keyboard and a user readable display. It might have an optical reader for reading bar codes or other optical indicia, in addition to other possible user interface devices and features. For example, a PDT can read one or more types of bar codes imprinted on a wristband according to the invention.

Figure 19:
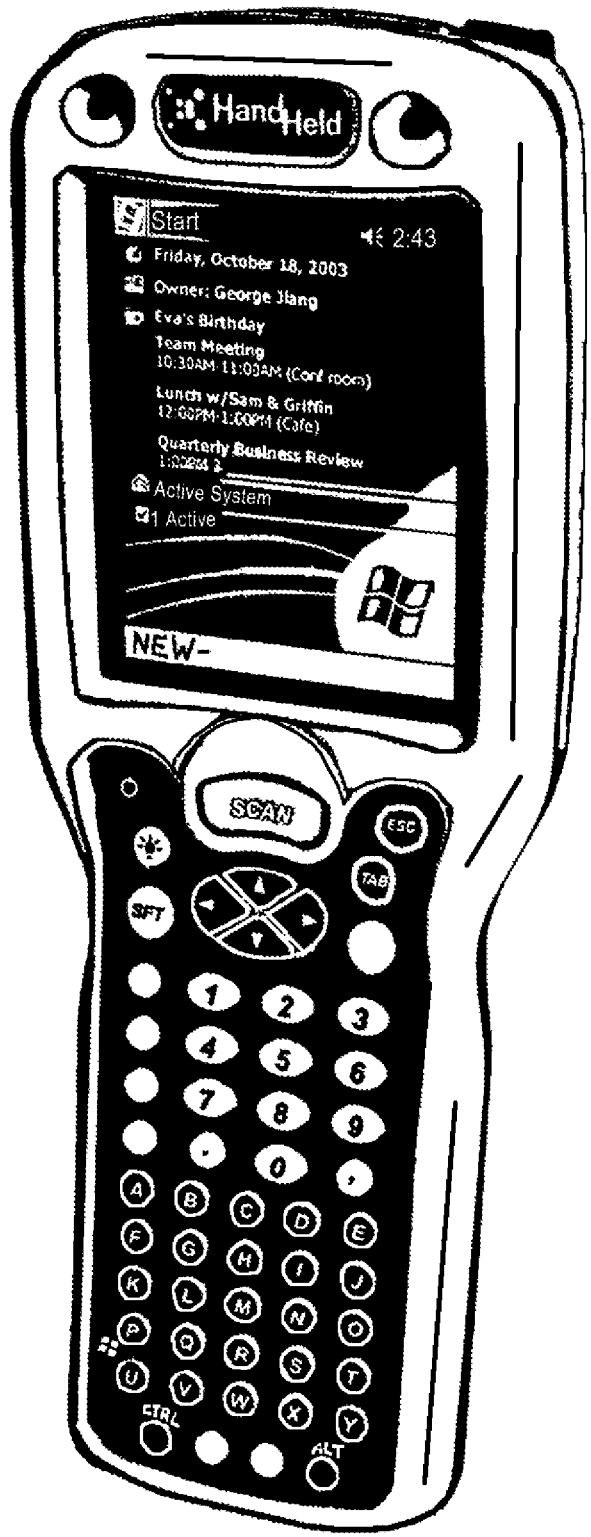
FIG. 19 shows an exemplary PDT manufactured by the HandHeld Products Corporation.

There are few differences between a (portable data terminal) PDT and a personal digital assistant (PDA). Similar to a PDA, a PDT typically runs an operating system such as Windows CE, a version of Windows optimized for small portable devices. Other small terminal operating systems, including proprietary operating systems can be suitable as well. An exemplary PDT is the Dolphin PDT manufactured by the HandHeld Products Corporation as shown in FIG. 19. A PDA can be a more general computational device while a PDT is typically slotted for a particular application. But, as both PDTs and PDAs continue to evolve, the line between them is becoming less clear. In fact the exemplary Dolphin PDT shown in FIG. 19 is essentially a Pocket PC running Windows CE. Therefore, for the purposes of this description, except for specific examples calling out a specific type of PDT, PDT and PDA can be considered to be interchangeable terms herein.

As PDTs have expanded in functionality to include data retrieval, both the users of data and persons to whom the data pertains to have become increasingly concerned with data security. To address these concerns, two additional security functions can be performed by a PDT operating in the inventive system. The first security features restrict access to the PDT to authorized users. In addition to providing access security to a PDT, this function can also cause a PDT to take on a custom configuration for each individual user. A second aspect of security applies to the protection of the data itself, including data read by the PDT, data contained within the PDT, and data that can be accessed by the PDT.

PDT access security (access to use the PDT) can be achieved in a variety of ways. Access methods and devices include smart cards, ID cards with barcodes, radio frequency ID ("RFID") cards and tags, and biometric identification devices. In the context of an exemplary hospital application, users to be identified by a PDT typically include nurses assistants, nurses, physician assistants, and doctors. In addition to granting access to a PDT, identification of a particular PDT user or class of users, can also limit the functionality of the PDT. Such functional limitations can be set for classes of users or for each individual user.

Figure 20A:
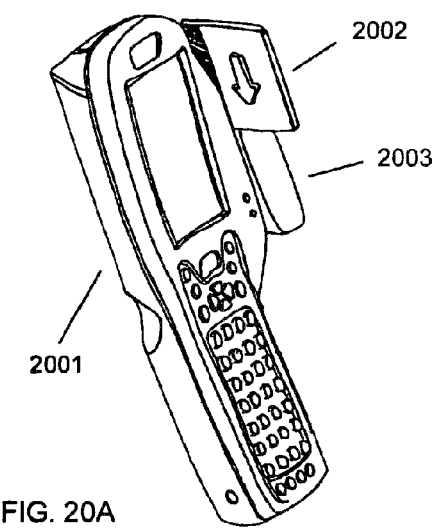
FIG. 20A shows an exemplary PDT having a card reader.
Figure 20B:
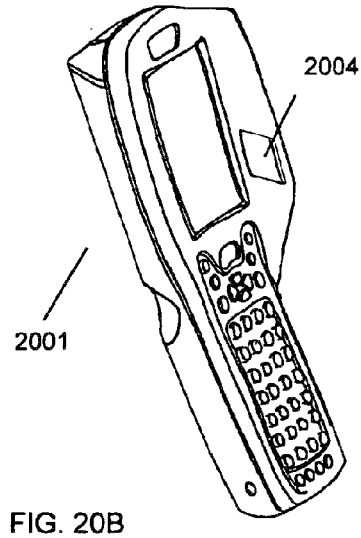
FIG. 20B shows an exemplary PDT having a finger print reader.

A PDT can identify a user by one of the aforementioned techniques, including smart cards, ID cards with barcodes, radio frequency ID ("RFID") cards or tags, and biometric identification devices. In the case of a smartcard, the PDT user can keep the card as a wallet card, or more conveniently wear the card on a lanyard around the user's neck as is now conventional practice for wearing and displaying ID cards. In this case as shown in FIG. 20A, a user of PDT 2001 can insert the card 2002 or swipe it a card reader 2003 or otherwise insert the card into a PDT smart card reader that can connect to the chip on a smartcard (not shown) such that the PDT could read the smart chip or a magnetic strip printed on the smart card.

On identifying the user and/or class of authorized user, the PDT can configure itself for that user. Configuration can include pertinent and authorized function menus and any personalized settings, including, custom menus, automatic entry of one or more ID fields to identify the PDT user who accessed and performed certain functions (including logs and logging) and or default fields such as the user's email address or the email address of the user's assistant, administrator, or supervisor. In the case of a user doctor, the PDT might also load certain fields with the doctor's registration number, prescription number, or other identification or authorization information.

Custom PDT configuration information associated with a particular user or class of users (such as nurses) can be stored in several locations. One or more configuration files can be stored in the PDT in any memory suitable for storage of configuration information. Or, the configuration information can be encoded within the identification media. For example, an identifying 2 D barcode printed on an ID card or wristband worn by the PDT user can store the PDT configuration data for that user. PDT configuration files can also reside on a hospital computer server or any other server accessible by the PDT via any network the PDT has access to in the hospital, including any network accessible by the Internet or equivalent network extending beyond the hospital.

Access to the PDT can also be granted by an RFID tag worn, carried by, or embedded in the prospective PDT user. The PDT can be connected to, or more conveniently include an internal RFID reader. On reading an individual's RFID tag, the PDT can grant access appropriate to a particular individual, a class of worker, or deny access to an unauthorized user. PDT access can also be granted or denied based on a biometric sensor connected to, or more desirably located within the PDT to identify a user by finger print for example. Finger print biometric identification can be done by a finger print imager, fingerprint scanner (including moving detectors, or by moving one's finger over a fixed array of detectors). Biometric scanners can also include human eye iris scanning While typically such units are conveniently wall mounted and would require a temporary wired connection to a PDT (such as an authorization "pig tail" wire hanging from a wall mounted sensor) or a wireless connection to the PDT, an iris scanner can be installed within a PDT as well. It is further contemplated as shown in FIG. 20D that sensors 2006 such as odor (electronic nose), chemical, and/or DNA sensors will likely be suitable for PDT 2001 identification as such sensor technologies further mature and become more widely commercially available.

It is also within the capability of a PDT to further employ an imager for entire body, partial body, or more conveniently facial recognition. Such imaging software for facial identification is presently in use and being further developed especially for identifying individuals in video surveillance images. Similar or simpler image recognition algorithms can be used for PDT access control.

Figure 21:
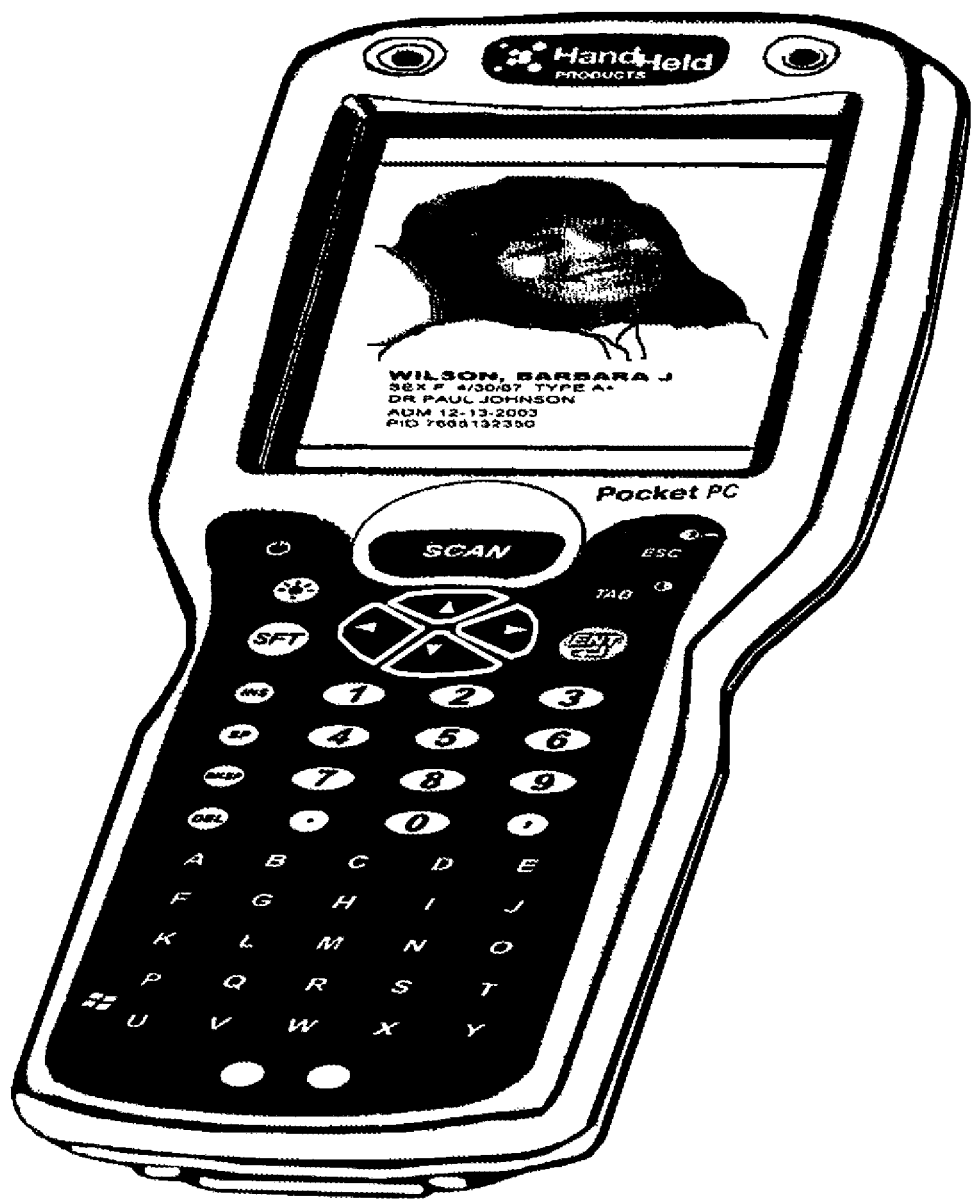
FIG. 21 shows a PDT displaying a simulated picture of an identified patient.

All of the aforementioned security access features can be applied to secure access to data. For example, a minimal data access authorization might allow a medical assistant only to identify a patient by reading a patient's bar coded wristband according to the invention. A PDT can also display a pre-stored image of the patient for additional verification of patient ID as shown in FIG. 21. Far more data or records, including patient history, personal information, medication, medication control, etc., might be available to a nurse or a doctor. In other words, such a data access system can be very conveniently setup in a "need to know" access system based on the identification of an individual user, or class of users. In such a data access system, a doctor, or only assigned doctors, might be the only PDT authorized users to have complete access to a patient's personal, information, medical history, etc.

Access control as described can also be used to ease the human—instrumentation interface in the hospital setting. For example, controllers that can administer settable dosages of medications via IV drips are well known. Using controlled PDT access through user identification, an authorized nurse, PA, or doctor can adjust and monitor the dosage from a PDT. Because of the natural computer functions of the PDT, an automatic signature of the administering individual can be logged along with the medication and dosage. Such logging can be integrated into an automated chart management function, drug usage logs, and can further include automatic monitoring of drug types, drug interactions, known patient allergies, and common dosage units suitable to particular drug types. Where a drug allergy, interaction, or incorrect dosage has been detected by the PDT, the PDT can refuse the command to the medical instrument, display the reason for the concern, and seek a new command or an override. Audile signals, alarms, or spoken electronic messages can also be used in such situations.

The administration of drugs to patients in general can be monitored by a PDT bar code reader using database information on board the PDT. For example, the PDT can check a dosage prescribed for a particular patient against a table of allowable dosages for each type of medication. The patients prescription can be entered into the PDT by keyboard, by reading a bar code, or by computer interface to another computer or a host computer that maintains prescription records. The PDT can also compare patient personal information against a prescribed medication to look for drug interactions or compare, for example a patient's weight to the recommended dosages by body weight for a particular medication. The databases containing the patient medication and personal information can reside in whole or in part on the PDT. Data not residing in the PDT can be acquired by the PDT by reading (OCR) characters or bar codes on the chart, medication containers, references, including reference books, or by communicating with an external host computer.

It should also be noted that in addition to any automated data logging as described herein, virtually all PDTs can also allow a user to further enter data pertaining to a patient, including a patient's condition, treatment, or medication, by manually entering data, comments, or completing forms using the PDT keyboard and any other available PDT manual entry device, such as an integral mouse and or mouse button (s). An integral mouse can take the form of a touch pad, eraser mouse, ball mouse, or other mouse functionality suitable to a PDT. Touch screens can also be used as PDT data entry devices.

A PDT or computer otherwise coupled to the PDT can also include setup and configuration information related to various medical devices. Such information can include device drivers and configuration information as well as digital communication modes available between the PDT and the device, including any appropriate wired and wireless standards as has been discussed herein. Medical instrument access and communication can further be secured through the use of secure keys and/or data encryption.

Figure 20C:
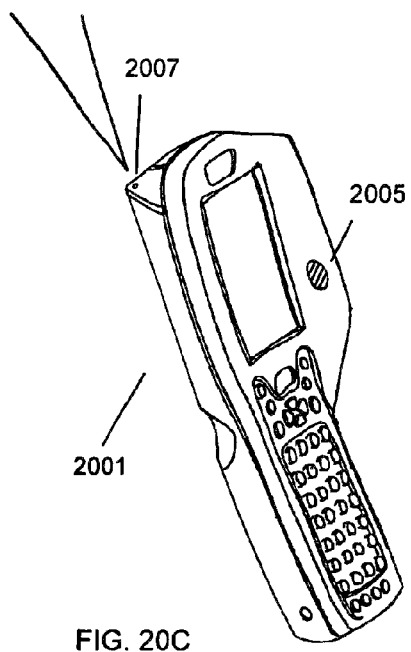
FIG. 20C shows an exemplary PDT having a UV LED and microphone.
Figure 20D:
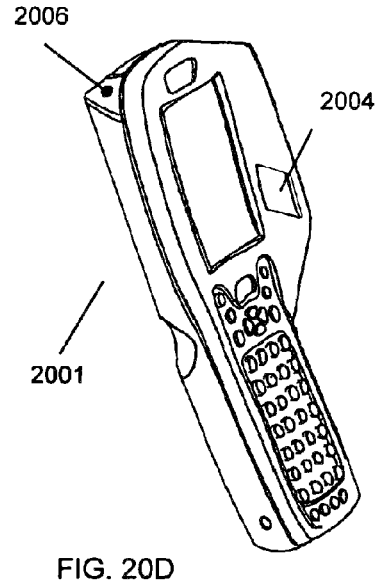
FIG. 20D shows an exemplary PDT having a chemical sensor (an electronic nose)

PDT 2001 for reading wristbands according to the invention can also incorporate a microphone 2005 as shown in FIG. 20C or receive a wireless microphone signal, or accept a plug from a wired microphone. The microphone can be used by an authorized PDT user to record information pertinent to the patient being treated and associated with the PDT user making the recording. Such recordings can include a practitioner's notes on treatment, condition, medication, etc. The PDT can also be used to record a dying declaration made by the wearer of the inventive bar coded wristband. Here, the PDT can be used to positively correlate the person speaking with wristband. Similarly the imager can be further used to record an image of the individual as well as one or more witnesses present to create a legal record. The imager on the PDT can similarly be used to further identify any person making an audio recording to the PDT with the microphone. In such as an integrated system has been described, it can further be seen that any dictation recorded by the PDT can be automatically associated the patient's file and/or any other patient records.

The imager function of a PDT can have other uses beyond reading bar coded wristbands for patient identification. For example, following an image of an inventive bar coded wristband and successful identification of the patient, any pertinent documents, printed cards, or other printed records can be recorded by the imager and associated with a patient.

When outfitted with certain additional devices, a PDT can further take on the role of a medical diagnostic instrument. For example as shown in FIG. 20C, with the addition of a controllable ultraviolet ("UV") light 2007, such as a UV light emitting diode (LED), the user of PDT 2001 can image various pathologies, including skin infections. Images thus derived can be used to assist in the diagnosis and progression of various ailments, and to create a record of the healing process. It is further contemplated that sensors, such as chemical sensors could similarly be used by a PDT in a diagnostic role.

Another use for the inventive multiple bar code system is to identify equipment and information related to the equipment. For example, a band or adhesive label having multiple bar codes can be affixed to a particular piece of equipment or instrumentation. Because of the inventive use of multiple bar code symbols it can be seen that reading can be conveniently done without having to move or reposition equipment. A multiple bar code band similar in style to a bar coded patient wristband can also be extended completely around any piece of equipment with larger dimensions than a patient wristband as needed to encompass any shape and size of equipment enclosure. The multiple bar coded equipment band or strip can further include calibration data for the equipment within the bar codes. A user can also access the appropriate version of the user manual for the equipment, the maintenance history, calibration history, etc., related to that equipment by using computer based bar code readers, such as the aforementioned PDTs. Other inventory functions, such as retrieving a list of where the equipment was found (or located) during past inventories can help return borrowed or misappropriated equipment to its rightful location or owner.

Included in the subject matter set forth herein in the following:

A1. A system to read a bar coded patient wristband to identify a patient wearing the wristband comprising:

a bar code reader to read the bar coded wristband, the bar code reader having a digital link to transmit a segment of data encoded in the bar code;

a host computer, the host computer connected to the digital link to receive the segment of data from the bar code reader;

a database coupled to the host computer via a digital connection, the database to correlate the segment of data to a patient record;

a patient wristband, the patient wristband comprising a plurality of 2 D bar code symbols, the plurality of bar code symbols containing information encoded into each bar code symbol, wherein the bar code reader reads at least one of the plurality of bar code symbols, the bar code reader transmitting the segment of data decoded from the at least one of the plurality of bar code symbols to the computer, and the computer retrieving the patient record from the database to identify the patient wearing the wristband.

A2. The system of A1 wherein the host computer is a local computer in a hospital.

A3. The system of A1 wherein the host computer is a remote computer on a computer network.

A4. The system of A1 wherein the database resides in a hospital.

A5. The system of A1 wherein the database resides outside of a hospital on a computer network.

A6. The system of A5 wherein the computer network is the Internet.

A7. The system of A1 wherein the digital link is a wireless digital link selected from the group of wireless digital links consisting of GSM, GPRS, EDGE, W-CDMA (FDD), HSDPA, TIA/EIA-95A/B, cdma2000, 1xEV-DO, 1xEV-DV, iDEN, TETRA, Bluetooth, PAN, IEEE 802.11 a/g/h/j, LAN, WAN, IEEE 802.15.3a, IEEE 802.16a/e, and MAN.

A8. The system of A7 wherein the digital link further comprises a link to the Internet.

A9. The system of A1 wherein a connection to the digital link is a wired digital link selected from the group of copper wire, coaxial cable, optical fiber, twisted wire, shielded cable, and shielded twisted wire.

A10. The system of A9 wherein the digital link is selected from the group of serial links consisting of RS-232, RS-485, parallel, USB, Ethernet, and Firewire.

A11. The system of A1 wherein the information encoded into each bar code symbol is selected from the group of information consisting of patient ID, patient name, patient address, current prescription medications, prescription history, medication history, and names of identifying physicians.

A12. The system of A1 wherein the information encoded into each bar code symbol complies with the HIBC standard indicating the type of data encoded and intended placement of the information on a patient wristband.

A13. The system of A1 wherein the information encoded into each bar code symbol incorporates a Health Industry Number (HIN) that identifies the institution that affixed the wristband.

A14. The system of A1 wherein the host computer alerts that a patient is overdue for a visit by a hospital employee.

A15. The system of A1 wherein the host computer monitors scans of patient wristbands and makes a report including patient visitation information to a hospital supervisor.

A16. The system of A1 wherein the bar code reader is a PDT.

A17. The system of A16 wherein the PDT further comprises a card reader for reading indicia on an ID card.

A18. The system of A17 wherein the indicia on the ID card is stored in a magnetic stripe and the card reader is a magnetic stripe card reader.

A19. The system of A16 wherein the PDT further comprises a biometric sensor to identify and grant PDT access to an identified and authorized user.

A20. The system of A19 wherein the biometric sensor is a fingerprint sensor.

A21. The system of A16 wherein the PDT further comprises a UV lamp to illuminate organs to highlight a pathological condition.

A22. The system of A21 wherein the UV lamp is a UV LED.

A23. The system of A16 wherein the PDT further comprises a microphone to record voice signals using the PDT.

A24. The system of A23 wherein the microphone is a wireless microphone.

A25. The system of A24 wherein the wireless microphone communicates according to the Bluetooth wireless communication standard.

A26. The system of A16 wherein the PDT further comprises a chemical sensor or electronic nose to analyze chemicals emitted from a human organ.

B1. A patient wristband for identifying a patient wearing the wristband comprising:

a substrate bendable strip, the strip bendable into a wristband, the substrate strip to accept a plurality of markings of 2 D bar codes distributed along the strip;

a closing mechanism, the closing mechanism to create a closed wristband from the bendable strip, wherein each of the plurality of markings of 2 D bar codes distributed along the strip contain encoded information to identify the patient wearing the wristband.

B2. The wristband of B1 wherein the 2 D bar codes are 2 D bar codes selected from the group consisting of Data Matrix, MicroPDF417, PDF417, and Aztec.

B3. The wristband of B1 wherein the wristband further comprises a section of human readable information.

B4. The wristband of B1 wherein the section of human readable information is printed over a row of Aztec 2 D bar code symbols.

B5. The wristband of B1 wherein the wristband comprises a single row of Aztec 2 D bar codes for pediatric applications.

B6. The wristband of B1 wherein the wristband comprises at least a single row of Aztec 2 D bar codes and at least one of the symbols remains readable even if the edge of the row is truncated by trimming the strip.

B7. The wristband of B1 wherein the wristband is printed on a wristband substrate material selected from the group of materials consisting of plastic, paper, mylar, aluminized mylar, foil, metal foil, metal, woven nylon, and woven cloth.

B8. The wristband of B1 wherein the plurality of markings of 2 D bar codes has a low level of reflectivity and the substrate has a higher level of reflectivity for an illumination wavelength.

B9. The wristband of B8 wherein the wristband substrate is a red or white wristband substrate.

B10. The wristband of B1 wherein the wristband comprises at least two holes for fastening the wristband to a limb.

B11. The wristband of B8 wherein the wristband further comprises a fastener for use with the at least two holes for fastening the wristband to a limb.

B12. The wristband of B 11 wherein the fastener is selected from the group of fasteners consisting of string, thread, wire, plastic filaments, tie wraps, plastic rivet, metal rivet, plastic clip, plastic screw and nut, metal screw and nut, and metal clip.

B13. The wristband of B1 wherein the plurality of markings of 2 D bar codes are printed by ink or thermal printing.

B14. The wristband of B1 wherein the plurality of markings of 2 D bar codes are printed in a color selected from the group of colors consisting of black, gray, blue, blue-green, and green.

C1. A patient wristband for identifying a patient wearing the wristband comprising:
  a substrate bendable strip, the strip bendable into a wristband, the substrate strip to accept a plurality of linear bar code lines and spaces distributed along the strip, the lines and spaces substantially aligned in a long narrow direction of the strip, the lines and spaces forming a 1 D bar code wherein an aspect ratio of height to width of the 1 D bar code is greater than 1;
  a closing mechanism, the closing mechanism to create a closed wristband from the bendable strip, wherein the plurality of linear bar code lines and spaces distributed along the strip can be read by a bar code reader from substantially any direction around the wristband to identify the patient wearing the wristband.

C2. The wristband of C1 wherein the wristband further comprises a section of human readable information.

C3. The wristband of C1 wherein the wristband is printed on a wristband substrate material selected from the group of materials consisting of plastic, paper, mylar, aluminized mylar, foil, metal foil, metal, woven nylon, and woven cloth.

C4. The wristband of C1 wherein the wristband comprises at least two holes for fastening the wristband to a limb.

C5. The wristband of C4 wherein the wristband further comprises a fastener for use with the at least two holes for fastening the wristband to a limb.

C6. The wristband of C5 wherein the fastener is selected from the group of fasteners consisting of string, thread, wire, plastic filaments, tie wraps, plastic rivet, metal rivet, plastic clip, plastic screw and nut, metal screw and nut, and metal clip.

C7. The wristband of C1 wherein the lines (bars) of the 1 D bar code have a low level of reflectivity and the substrate has a higher level of reflectivity for an illumination wavelength.

C8. The wristband of C7 wherein the 1 D bar code is printed by ink or thermal printing.

C9. The wristband of C8 wherein the 1 D bar code is printed in a color selected from the group of colors consisting of black, gray, blue, blue-green, and green.

C10. The wristband of C1 wherein the aspect ratio of height to width of the 1 D bar code is sufficiently large such that the lines and spaces of the barcode extend substantially across an entire lengthwise (long) direction of the wristband without gaps other than at a closing edge.

D1. A system to read a bar coded patient wristband to identify a patient wearing the wristband comprising:
  a bar code reader to read the bar coded wristband;
  a housing to hold the bar code reader;
  a computer contained within the housing, the computer connected to the bar code reader to receive a segment of data from the bar code reader;
  a patient wristband, the patient wristband comprising a plurality of 2 D bar code symbols, the plurality of bar code symbols containing information encoded into each bar code symbol, wherein the bar code reader reads at least one of the plurality of bar code symbols, the bar code reader transmitting the segment of data decoded from the at least one of the plurality of bar code symbols to the computer, and the computer identifying the patient wearing the wristband.

D2. The system of D1 further comprising a database contained within the housing and coupled to the computer, the database to correlate the segment of data to a patient record.

D3. The system of D2 wherein the identification of the patient is correlated to at least one item of information in the patient record to reduce hospital errors for the purpose of enhancing patient safety.

D4. The system of D2 wherein the database in the housing can be updated by a host computer using a digital link to the computer in the bar code reader.

D5. The system of D2 wherein the database in the housing can be updated by a host computer outside of a hospital using a computer network connected to the computer in the bar code reader housing.

D6. The system of D5 wherein the computer network is the Internet.

D7. The system of D4 wherein the digital link is a wireless digital link selected from the group of wireless digital links consisting of GSM, GPRS, EDGE, W-CDMA (FDD), HSDPA, TIA/EIA-95A/B, cdma2000, 1xEV-DO, 1xEV-DV, iDEN, TETRA, Bluetooth, PAN, IEEE 802.11 a/g/h/j, LAN, WAN, IEEE 802.15.3a, IEEE 802.16a/e, and MAN.

D8. The system of D7 wherein the digital link further comprises a link to the Internet.

D9. The system of D4 wherein a connection to the digital link is a wired digital link selected from the group of copper wire, coaxial cable, optical fiber, twisted wire, shielded cable, and shielded twisted wire.

D10. The system of D9 wherein the digital link is selected from the group of serial links consisting of RS-232, RS-485, parallel, USB, Ethernet, and Firewire.

D11. The system of D1 wherein the information encoded into each bar code symbol is selected from the group of information consisting of patient ID, patient name, patient address, current prescription medications, prescription history, medication history, and names of identifying physicians.

D12. The system of D1 wherein the information encoded into each bar code symbol complies with the HIBC standard indicating the type of data encoded and intended placement of the information on a patient wristband.

D13. The system of D1 wherein the information encoded into each bar code symbol incorporates a Health Industry Number (HIN) that identifies the institution that affixed the wristband.

D14. The system of D4 wherein the host computer alerts that a patient is overdue for a visit by a hospital employee.

D15. The system of D4 wherein the host computer monitors scans of patient wristbands and makes a report including patient visitation information to a hospital supervisor.
D16. The system of D1 wherein the bar code reader is a PDT.
D17. The system of D16 wherein the PDT further comprises a card reader for reading indicia on an ID card.
D18. The system of D17 wherein the indicia on the ID card is stored in a magnetic stripe and the card reader is a magnetic stripe card reader.
D19. The system of D16 wherein the PDT further comprises a biometric sensor to identify and grant PDT access to an identified and authorized user.
D20. The system of D19 wherein the biometric sensor is a fingerprint sensor.
D21. The system of D16 wherein the PDT further comprises a UV lamp to illuminate organs to highlight a pathological condition.
D22. The system of D21 wherein the UV lamp is a UV LED.
D23. The system of D16 wherein the PDT further comprises a microphone to record voice signals using the PDT.
D24. The system of D23 wherein the microphone is a wireless microphone.
D25. The system of D24 wherein the wireless microphone communicates according to the Bluetooth wireless communication standard.
D26. The system of D26 wherein the PDT further comprises a chemical sensor or electronic nose to analyze chemicals emitted from a human organ.

While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A system for reading a bar coded patient wristband, the system comprising:
    a bar code reading portable data terminal (PDT) communicatively coupled to a computer;
    a database communicatively coupled to the computer;
    a patient wristband comprising a plurality of 2 D bar code symbols, the plurality of bar code symbols containing information encoded into each bar code symbol;
    wherein the bar code reading PDT is configured to read at least one of the plurality of bar code symbols and transmit data decoded from the at least one of the plurality of bar code symbols to the computer,
    wherein the computer is configured to retrieve a patient record from the database based on at least a segment of the data decoded and transmit one or more items of the patient record to the bar code reading PDT;
    wherein the system is configured to display one or more items of the patient record;
    wherein the bar code reading PDT is configured for authentication of a user operating the bar code reading PDT, and wherein the authentication is characterized by one or more of (a) the authentication uses an output of a reader or sensor of the bar code reading PDT, and (b) the authentication comprises performing biometric based identification of the user; and wherein the system is configured to only display those items of the patient record which the user is authorized based on the authentication by the bar code reading PDT to access.

2. The system of claim 1, wherein the computer is provided by a local computer in a hospital.

3. The system of claim 1, wherein the computer is provided by a remote computer on a computer network.

4. The system of claim 1, wherein the database resides in a hospital.

5. The system of claim 1, wherein the database resides outside of a hospital on a computer network.

6. The system of claim 1, wherein the information encoded into each bar code symbol includes at least one of: patient ID, patient name, patient address, current prescription medications, prescription history, medication history, and names of identifying physicians.

7. The system of claim 1, wherein the information encoded into each bar code symbol complies with the HIBC standard indicating a type of data encoded and intended placement of the information on a patient wristband.

8. The system of claim 1, wherein the information encoded into each bar code symbol incorporates a Health Industry Number (HIN) that identifies an institution that affixed the wristband.

9. The system of claim 1, wherein the host computer is configured to alert that a patient is overdue for a visit by a hospital employee.

10. The system of claim 1, wherein the host computer is configured to monitor scans of patient wristbands and makes a report including patient visitation information to a hospital supervisor.

11. The system of claim 1, wherein the bar code reading PDT further comprises a card reader for reading indicia on an ID card.

12. The system of claim 11, wherein the indicia on the ID card is stored in a magnetic stripe and the card reader is a magnetic stripe card reader.

13. The system of claim 1, wherein the bar code reading PDT is further configured to authenticate said user using a biometric sensor.

14. The system of claim 13, wherein the biometric sensor is provided by a fingerprint sensor.

15. The system of claim 1, wherein the bar code reading PDT further comprises a UV lamp.

16. The system of claim 15, wherein the UV lamp is provided by a UV LED.

17. The system of claim 1, wherein the bar code reading PDT further comprises a microphone to record voice signals using the bar code reading PDT.

18. The system of claim 17, wherein the microphone is a wireless microphone.

19. The system of claim 18, wherein the wireless microphone communicates according to the Bluetooth wireless communication standard.

20. The system of claim 1, wherein the bar code reading PDT further comprises a chemical sensor or electronic nose to analyze chemicals emitted from a human organ.

21. The system of claim 1, wherein the database is configured to be updated by an external computer.

22. The system of claim 1, wherein all bar code symbols of said plurality of 2 D bar code symbols are identical.

23. The system of claim 1, wherein said plurality of 2 D bar code symbols comprises bar code symbols of different types.

24. The system of claim 1, wherein the computer is provided by at least one of: a computer collocated with the bar code reading PDT in a single housing, an external computer.

25. The system of claim 1, wherein the authentication is characterized by: the authentication uses an output of a reader or sensor of the bar code reading PDT.

26. The system of claim 1, wherein the authentication is characterized by: the authentication comprises performing biometric based identification of the user.

* * * * *